(12) United States Patent
Feitelson

(10) Patent No.: US 11,963,938 B2
(45) Date of Patent: Apr. 23, 2024

(54) USE OF SHORT CHAIN FATTY ACIDS IN CANCER PREVENTION

(71) Applicant: Temple University-Of The Commonwealth System of Higher Education, Philadelphia, PA (US)

(72) Inventor: Mark A. Feitelson, North Wales, PA (US)

(73) Assignee: Temple University-Of The Commonwealth System of Higher Education, Philadelphia, PA (US)

( * ) Notice: Subject to any disclaimer, the term of this patent is extended or adjusted under 35 U.S.C. 154(b) by 40 days.

(21) Appl. No.: 17/379,305

(22) Filed: Jul. 19, 2021

(65) Prior Publication Data

US 2022/0008369 A1     Jan. 13, 2022

Related U.S. Application Data

(63) Continuation of application No. 16/261,836, filed on Jan. 30, 2019, now abandoned, which is a
(Continued)

(51) Int. Cl.
*A61K 31/19*     (2006.01)
*A61K 9/00*     (2006.01)
(Continued)

(52) U.S. Cl.
CPC ............ *A61K 31/19* (2013.01); *A61K 9/0053* (2013.01); *A61K 35/744* (2013.01); *A61K 35/747* (2013.01); *A61P 35/00* (2018.01)

(58) Field of Classification Search
CPC .................................................... A61K 31/19
See application file for complete search history.

(56) References Cited

U.S. PATENT DOCUMENTS

| 4,735,967 A | 4/1988 | Neesby |
| 5,919,822 A | 7/1999 | Cotter |

(Continued)

FOREIGN PATENT DOCUMENTS

| CN | 101214234 A | 7/2008 |
| CN | 103037691 | 4/2013 |

(Continued)

OTHER PUBLICATIONS

Raso et al., "Effects of sodium butyrate and its synthetic amide derivative on liver inflammation and glucose tolerance in an animal model of steatosis induced by high fat diet," PLOS One 8(7):1-15, e6862.*

(Continued)

*Primary Examiner* — Rosanne Kosson
(74) *Attorney, Agent, or Firm* — Riverside Law LLP

(57) ABSTRACT

The invention relates to compositions for preventing or delaying the onset of hepatocellular cancer. The compositions of the invention may comprise short chain fatty acids. The compositions of the invention may also comprise probiotic bacteria. The compositions of the invention include compositions for preventing or delaying the onset of hepatocellular cancer by treating or preventing liver inflammation, liver disease, and precancerous lesions.

17 Claims, 10 Drawing Sheets

Related U.S. Application Data continuation of application No. 15/545,371, filed as application No. PCT/US2016/014292 on Jan. 21, 2016, now Pat. No. 10,231,941.

(60) Provisional application No. 62/106,778, filed on Jan. 23, 2015.

(51) Int. Cl.
    *A61K 35/744* (2015.01)
    *A61K 35/747* (2015.01)
    *A61P 35/00* (2006.01)

(56) References Cited

U.S. PATENT DOCUMENTS

| | | |
|---|---|---|
| 7,029,669 B1 | 4/2006 | Reniero |
| 7,303,889 B2 | 12/2007 | Lepoul |
| 7,399,787 B2 | 7/2008 | Chiao |
| 9,764,019 B2 | 9/2017 | Honda |
| 2004/0018968 A1 | 1/2004 | Sgouros |
| 2004/0024160 A1 | 3/2004 | Wo |
| 2004/0127523 A1 | 7/2004 | Bacopoulos |
| 2005/0023179 A1 | 3/2005 | Wo |
| 2008/0107646 A1 | 5/2008 | Chung |
| 2011/0118217 A1 | 5/2011 | Gudmundsson |
| 2011/0300238 A1 | 12/2011 | Eritzland |
| 2013/0115280 A1 | 5/2013 | Moro |
| 2013/0323215 A1 | 12/2013 | Foo |
| 2014/0065114 A1 | 3/2014 | Lin |

FOREIGN PATENT DOCUMENTS

| | | |
|---|---|---|
| JP | 2000072667 | 3/2000 |
| JP | 2014047212 | 3/2014 |
| JP | 2014506923 A | 3/2014 |
| WO | 1992015292 A1 | 9/1992 |
| WO | 1995011699 A1 | 5/1995 |
| WO | 19950011699 | 5/1995 |
| WO | 2004024160 A1 | 3/2004 |
| WO | 2005023179 A2 | 3/2005 |
| WO | 2007016953 A1 | 2/2007 |
| WO | 2007114697 A1 | 10/2007 |
| WO | 2008079697 | 7/2008 |
| WO | 2010146568 A1 | 12/2010 |
| WO | 2011137173 | 11/2011 |
| WO | 2011147585 | 12/2011 |
| WO | 2012013495 A1 | 2/2012 |
| WO | 2012131069 | 10/2012 |
| WO | 2013109635 A1 | 7/2013 |
| WO | 2014033453 A1 | 3/2014 |
| WO | 2015006355 | 1/2015 |
| WO | 2015021936 A1 | 2/2015 |

OTHER PUBLICATIONS

Jakobsdottir et al., High-fat diet reduces the formation of butyrate, but increases succinate, inflammation, liver fat and cholesterol in rats, while dietary fiber counteracts these effects, PLOS One 8(11):1-15, e80476.*
Mily A, Rekha RS, Kamal SM, et al. Significant Effects of Oral Phenylbutyrate and Vitamin D3 Adjunctive Therapy in Pulmonary Tuberculosis: A Randomized Controlled Trial. PLoS One. 2015; 10(9):e0138340, 25 pages.
Usami M, Kishimoto K, Ohata A, et al., "Butyrate and trichostatin A attenuate nuclear factor kappaB activation and tumor necrosis factor alpha secretion and increase prostaglandin E2 secretion in human peripheral blood mononuclear cells," Nutr Res. 2008;28(5):321-328.
A De Conti et al: "The chemopreventive activity of the butyric acid prodrug tributyrin in experimental rat hepatocarcinogenesis is associated with p53 acetylation and activation of the p53 apoptotic signaling pathway", Carcinogenesis, vol. 34, No. 8: pp. 1900-1906 (Apr. 8, 2013).
Astakhova et al., "Short Chain Fatty Acids (SCFA) Reprogram Gene Expression in Human Malignant Epithelial and Lymphoid Cells", 2016, PLOS one, 11(7):e0154102: pp. 1-18.
Bindels et al., 2012, Gut microbiota-derived propionate reduces cancer cell proliferation in the liver, Br J Cancer, 107 8):1337-44.
Bindels et al., 2013, GPR43/FFA2: physiopathological relevance and therapeutic prospects, Trends Pharmacol Sci, 34(4):226-32.
Calcium propionate (282), GSFA Online, Food Additive Details, Codex Alimentarius, https://web.archive.org/web/20061021214228/http://www.codexalimentarius.net/gsfaonline/additives/details.html?id=306, 2006.
Canani et al., "The epigenetic effects of butyrate: potential therapeutic implications for clinical practice", Clinical Epigenetics, 2012; vol. 4(4):pp. 1-7.
Celasco et al., 2014, Calcium butyrate: Anti-inflammatory effect on experimental colitis in rats and antitumor properties, Biomed Rep, 2(4):559-563.
Chinese Office Action (with English language translation) for Application No. CN201680017250.3, dated Dec. 12, 2019, 13 pages.
Cotto et al., "Epigenetic therapy of lymphoma using histone deacetylase inhibitors", 2010, Clin Transl Oncol, 12:401-409.
De Conti et al., 2012, Chemopreventive effects of the dietary histone deacetylase inhibitor tributyrin alone or in combination with vitamin A during the promotion phase of rat hepatocarcinogenesis, J Nutr Biochem, 23(8):860-6.
Endo et al., 2013, Butyrate-Producing Probiotics Reduce Nonalcoholic Fatty Liver Disease Progression in Rats: New insight into the Probiotics for the Gut-Liver Axis, PLoS ONE, 8(5):e63388.
European Extended Search Report and Written Opinion dated Sep. 6, 2018, issued in EP Application No. EP16740745.1, 15 pages.
Feitelson et al., 1997, Hepatitis B Virus x Antigen in the Pathogenesis of Chronic Infections and the Development of Hepatocellular Carcinoma, Amer J Pathol, 150:1141-1157.
Flores et al., 2014, Emerging Trends in Hepatocellular Carcinoma: Focus on Diagnosis and Therapeutics, Clin Med Insights Oncol, 8:71-6.
Israel Office Action for Application No. IL253581, dated Nov. 28, 2019, 3 pages.
Japanese Office Action (with English language translation) for Application No. JP2017-557279, dated Oct. 31, 2019, 8 pages.
Joo et al., "Enteral supplement enriched with glutamine, fiber and oligosaccharide attenuates experimental colitis in mice," Nutrition 29:549-555, 2013.
Kiefer et al., "Mixtures of SCFA, composed according to physiologically available concentrations in the gut lumen, modulate histone acetylation in human HT29 colon cancer cells", British Journal of Nutrition (2006), 96, 803-810.
Kunihiko Ohnishi et al: "Prospective randomized controlled trial comparing percutaneous acetic acid injection and percutaneous ethanol injection for small hepatocellular carcinoma", H Epatology, vol. 27, No. 1, Jan. 1, 1998 (Jan. 1, 1998), pp. 67-72.
Kuroiwa-Trzmielina et al., 2009, Chemoprevention of rat hepatocarcinogenesis with histone deacetylase inhibitors: Efficacy of tributyrin, a butyric acid prodrug, Int J Cancer, 124(11):2520-7.
Mann, 2014, Epigenetics in Liver Disease, Hepatology 60(4):1418-1425.
Mattace Raso Giuseppina et al: "Effects of a Lactobacillus paracaseiB21060 based synbiotic on steatosis, insulin signaling and toll-like receptor expression in rats fed a high-fat diet", The Journal of Nutritional Biochemistry, vol. 25, No. 1: pp. 81-90 (Jan. 2014).
McBain et al., "Apoptotic Death in Adenocarcinoma Cell Lines Induced by Butyrate and Other Histone Deacetylase inhibitors", Biochemical Pharmacology, vol. 53, pp. 1357-1368, (1997).
Menne et al., 2007, The woodchuck as an animal model for pathogenesis and therapy of chronic hepatitis B virus infection, World J Gastroenterol, 13(1):104-24.

(56) References Cited

OTHER PUBLICATIONS

Merzvinskyte et al., "Effects of Histone Deacetylase Inhibitors, Sodium Phenyl Butyrate and Vitamin B3, in Combination with Retinoic Acid on Granulocytic Differentiation of Human Promyelocytic Leukemia HL-60 Cells", Ann. N.Y. Acad. Sci. 1091: 356-367 (2006).

Mori, "Inhibition of Experimental Production of Liver Cancer by Addition of Acetic Acid to the Diet," Gann, 1953, vol. 44, No. 4, pp. 429-435.

Notice of Allowance dated Dec. 19, 2018 for U.S. Appl. No. 15/545,371 (pp. 1-8).

Notice of Allowance dated Oct. 12, 2018 for U.S. Appl. No. 15/903,395 (pp. 1-7).

Ogawa et al., "Sodium butyrate inhibits angiogenesis of human intestinal microvascular endothelial cells through COX-2 inhibition", FEBS Lett. 2003;554(1-2):88-94.

Park et al., 2015, Short chain fatty acids induce both effector and regulatory T cells by suppression of histone deacetylases and regulation of the mTOR-S6K pathway, Mucosal Immunol, 8(1):80-93.

Parodi, "Cow's milk components with anti-cancer potential", Australian Journal of Dairy Technology; Jul. 2001; vol. 56, No. 2: ProQuest; pp. 65-73.

Peck-Radosavljevic, 2014, Drug Therapy for Advanced-Stage Liver Cancer, Liver Cancer, 3(2):125-31.

Raso et al., 2013, Effects of Sodium Butyrate and Its Synthetic Amide Derivative on Liver Inflammation and Glucose Tolerance in an Animal Model of Steatosis Induced by High Fat Diet, PLoS ONE 8(7):e68626.

Russian Office Action (with English language translation) for Application No. 2017127597, dated Jun. 27, 2019, 12 pages.

Russian Office Action (with English language translation) for Application No. 2017127597, dated Nov. 15, 2019, 17 pages.

Santini et al., "Induction of apoptosis by monosaccharide butyrate derivatives in chronic lymphocytic leukemia cells", Haematologica, 1999; vol. 84: 897-904.

Sivan et al., Hubert N. Commensal Bifidobacterium promotes antitumor immunity and facilitates anti-PD-L1 efficacy. Science. 2015; vol. 350:1084-1089.

Smith et al., 2013, The microbial metabolites, short chain fatty acids, regulate colonic Treg cell homeostasis, Science, 341(6145):569-73.

Stephen M. Riordan et al: "Synbiotic-associated improvement in liver function in cirrhotic patients: Relation to changes in circulating cytokine messenger RNA and protein levels", Microbial Ecology in Health and Disease, vol. 19, No. 1, Jan. 1, 2007 (Jan. 1, 2007), pp. 7-16.

T. Eslamparast et al: "Synbiotic supplementation in nonalcoholic fatty liver disease: a randomized. double-blind, placebo-controlled pilot study", The American Journal of Clinical Nutrition, vol. 99, No. 3: pp. 535-542 (Jan. 8, 2014).

Tan et al., 2014, The Role of Short-Chain Fatty Acids in Health and Disease, Adv Immunol, 121:91-119.

Tian et al., 2013, Hepatitis B Virus X Protein-Induced Aberrant Epigenetic Modifications Contributing to Human Hepatocellular Carcinoma Pathogenesis, Mol Cell Biol, 33(15):2810-6.

Vinolo et al., "Suppressive effects of short-chain fatty acids on production of proinflammatory mediators by neutrophils," J Nutritional Biochemistry 22: 849-855, 2011.

Wan-Chun Chiu et al: "Synbiotics reduce ethanol-induced hepatic steatosis and inflammation by improving intestinal permeability and microbiota in rats", Food & Function, vol. 6, No. 5, Jan. 1, 2015 (Jan. 1, 2015), pp. 1692-1700.

Wang et al., "Anticancer effects of sodium butyrate on hepatocellular carcinoma cells in vitro," International Journal of Molecular Medicine 31:967-974, 2013.

Watkins S M et al: "Butyric acid and tributyrin induce apoptosis in human hepatic tumour cells.", The Journal of Dairy Research Nov. 1999, vol. 66, No. 4, Nov. 1999 (Nov. 1999), pp. 559-567.

Yoo et al., 2008, Hepatitis B virus X protein induces the expression of MTA1 and HDAC1, which enhances hypoxia Signaling in hepatocellular carcinoma cells, Oncogene, 27:3405-13.

Zhang et al: "Profound impact of gut homeostasis on chemically-induced pro-tumorigenic inflammation and hepatocarcinogenesis in rats", Journal of Hepatology, vol. 57, No. 4: pp. 803-812 (Oct. 1, 2012).

Van Kampen et al., "Epigenetic Targeting in Pancreatic Cancer" Cancer Treatment Reviews, 2014, 40:656-664.

* cited by examiner

Liver pathology in HBx mice treated with Symbiotic 2000 from mo. 3-6.

| PBS | | | | | | Symbiotic 2000 | | | | | |
|---|---|---|---|---|---|---|---|---|---|---|---|
| mouse no. | NSL | CH | stea-tosis | dys-plasia | HCC | mouse no. | NSL | CH | stea-tosis | dys-plasia | HCC |
| 668 | + | - | - | - | - | 687 | + | - | - | - | - |
| 673 | + | - | - | - | - | 689 | + | - | - | - | - |
| 669 | - | + | + | - | - | 657 | + | - | - | - | - |
| 671 | - | + | + | - | - | 659 | + | - | - | - | - |
| 675 | - | + | + | - | - | 672 | - | + | - | - | - |
| 708 | - | + | - | - | - | 676 | + | - | - | - | - |
| 712 | - | + | - | - | - | 684 | - | + | - | - | - |
| 713 | + | - | - | - | - | 693 | - | + | - | - | - |
| 714 | - | - | + | - | - | 701 | + | - | - | - | - |
| 715 | + | - | - | - | - | 704 | - | + | - | - | - |
| totals | 4 | 5 | 1 | 0 | 0 | | 6 | 4 | 0 | 0 | 0 |
| % | 40 | 50 | 10 | 0 | 0 | | 60 | 40 | 0 | 0 | 0 |

NSL = no significant lesions, CH = chronic hepatitis, Steatosis = fatty liver, dysplasia = islands or nodules of dysplastic cells (large nuclear cytoplasmic ratio), HCC = hepatocellular carcinoma.

Figure 7

Liver pathology in HBx mice treated with Symbiotic 2000 from mo. 6-9.

| PBS | | | | | | Symbiotic 2000 | | | | | |
|---|---|---|---|---|---|---|---|---|---|---|---|
| mouse no. | NSL | CH | stea-tosis | dys-plasia | HCC | mouse no. | NSL | CH | stea-tosis | dys-plasia | HCC |
| 475 | - | - | - | + | - | 617 | - | - | - | + | - |
| 476 | - | - | - | + | - | 627 | + | - | - | - | - |
| 477 | - | - | - | + | - | 637 | - | - | - | + | - |
| 479 | - | - | - | + | - | 652 | + | - | - | + | - |
| 480 | - | - | - | + | - | 653 | + | - | - | - | - |
| 481 | - | - | - | + | - | 621 | + | - | - | - | - |
| 482 | - | - | - | + | - | 629 | - | - | + | - | - |
| 483 | - | - | - | + | - | 630 | + | - | - | - | - |
| 484 | - | - | - | + | - | 631 | - | - | - | - | - |
| 485 | - | - | - | + | - | 647 | - | - | - | + | - |
| totals | 0 | 0 | 0 | 10 | 0 | | 5 | 0 | 1 | 4 | 0 |
| % | 0 | 0 | 0 | 100 | 0 | | 50 | 0 | 10 | 40 | 0 |

For abbreviations, please see the key to Figure 7.

Figure 8

Liver pathology in HBx mice treated with Symbiotic 2000 from mo. 9-12

| | PBS | | | | | | Symbiotic 2000 | | | | | |
|---|---|---|---|---|---|---|---|---|---|---|---|---|
| mouse no. | NSL | CH | stea-tosis | dys-plasia | HCC | | mouse no. | NSL | CH | stea-tosis | dys-plasia | HCC |
| 304 | - | - | - | +* | +* | | 414 | - | - | - | + | - |
| 319 | - | - | + | +* | +* | | 360 | - | - | + | +* | - |
| 290 | - | - | - | + | - | | 336 | - | - | - | +* | - |
| 326 | - | - | - | + | +* | | 287 | - | + | + | +* | +* |
| 374 | - | - | + | +* | +* | | 364 | - | - | + | + | +* |
| 344 | - | - | + | +* | +* | | 325 | - | + | + | - | +* |
| 285 | - | - | - | +* | +* | | 327 | - | - | - | - | - |
| 289 | - | - | + | +* | +* | | 397 | - | - | - | + | +* |
| 308 | - | - | + | +* | +* | | 331 | - | - | + | + | - |
| 363 | - | - | + | +* | +* | | 371 | - | - | + | + | - |
| totals | 0 | 0 | 5 | 10 | 9 | | | 0 | 2 | 8 | 9 | 4 |
| % | 0 | 0 | 50 | 100 | 90 | | | 0 | 20 | 80 | 90 | 40 |

For abbreviations, please see the key to Figure 7.
The asterisk (*) refers to samples with multiple and/or large nodules of dysplasia or HCC.

Figure 9

Intrahepatic HBx staining in Symbiotic 2000 treated and control mice

| | % positive (mice) | intensity of staining | tissue distribution |
|---|---|---|---|
| 3 mo. old mice | | | |
| + Symbiotic 2000 | 46 | - → + | mostly scattered |
| - Symbiotic 2000 | 60 | + → ++ | scattered/lobular |
| 6 mo. old mice | | | |
| + Symbiotic 2000 | 59 | + → ++ | scattered |
| - Symbiotic 2000 | 82 | ++ | lobular |
| 9 mo. old mice | | | |
| + Symbiotic 2000 | 66 | + → ++ | lobular |
| - Symbiotic 2000 | 100 | ++ → +++ | lobular → diffuse |

Presence, frequency and distribution of HBx in the livers of HBx transgenic mice fed Symbiotic 2000 (+ Symbiotic 2000) or PBS (- Symbiotic 2000).

Figure 10

USE OF SHORT CHAIN FATTY ACIDS IN CANCER PREVENTION

CROSS-REFERENCE TO RELATED APPLICATIONS

This application is a Continuation of U.S. application Ser. No. 16/261,836 filed on Jan. 30, 2019, which is a Continuation of U.S. application Ser. No. 15/545,371 filed on Jul. 21, 2017 claiming benefit to International Patent Application No. PCT/US2016/014292, filed on Jan. 21, 2016, which is entitled to priority under 35 U.S.C. § 119(e) to U.S. provisional application No. 62/106,778, filed Jan. 23, 2015, the disclosures of which are incorporated herein by reference in their entirety.

BACKGROUND OF THE INVENTION

Hepatocellular carcinoma (HCC) is the fifth most prevalent cancer and second leading cause of cancer deaths worldwide (Ding J et al., Cancer Lett, 2014; 346(1):17-23). Early HCC is frequently asymptomatic, where curative approaches could be applied, and by the time advanced disease is detected, few treatment options are available. The survival for untreated HCC is less than 3% over 5 years, and even with the application of the multi-kinase inhibitor sorafenib, life expectancy has only been extended for an average of 3 months (Peck-Radosavljevic M, Liver Cancer, 2014; 3(2):125-31). Combination therapy using sorafenib plus cytotoxic drugs has extended the life span to almost a year following diagnosis.

HCC most often arises in a background of persistent inflammation (hepatitis), and is frequently associated with chronic hepatitis B and C virus infections (Flores et al., Clin Med Insights Oncol, 2014; 8:71-6). For hepatitis B virus (HBV), the centrality of chronic liver disease (CLD) to the pathogenesis of HCC is highlighted in the related woodchuck hepatitis virus (WHV) model (Menne S et al., World J Gastroenterol, 2007; 13(1):104-24). In this case, chronic WHV infection and CLD resulted in nearly 100% incidence of HCC, while only a few percent of woodchucks with acute, resolving infections developed this tumor (Menne S et al., World J Gastroenterol, 2007; 13(1):104-24). Likewise, patients who are virus carriers with progressive chronic liver disease (hepatitis, fibrosis, and then cirrhosis) are at high risk for HCC, while asymptomatic carriers are at a much lower risk (Beasley et al., Lancet, 1981; 2(8256):1129-33). HBV and related mammalian hepadnaviruses (including WHV) encode a small polypeptide, referred to as X antigen, which contributes importantly to the pathogenesis of HCC (Feitelson M A et al., Amer J Pathol, 1997; 150:1141-1157). HBV encoded X antigen, or HBx, is a trans-regulatory protein that alters patterns of host gene expression by constitutively activating signaling pathways in the cytoplasm and by binding to complexes that regulate gene transcription in the nucleus (Tian Y et al., Mol Cell Biol, 2013; 33(15):2810-6; Feitelson M A et al., Amer J Pathol, 1997; 150:1141-1157). Integration of the HBx gene occurs in most chromosomes, and such integration events accumulate with each bout of hepatitis and regeneration, resulting in increased intracellular accumulation of HBx (Xu C et al., Cancer Lett, 2014; 345(2):216-22; Wang W et al., Hepatology, 1998; 14:29-37; Wang W et al., Cancer Res, 1991; 51:4971-4977). HBx promotes cell survival and growth in the face of cell mediated immune responses aimed at damaging and killing virus infected cells. Thus, there is a close association between HBx and CLD (Jin Y M et al., J Viral Hepat, 2001; 8(5):322-30). In this context, HBx appears to be activated by free radicals (Wang J H et al., Biochem Biophys Res Commun, 2003; 310(1):32-9) generated by immune responses aimed at virus infected hepatocytes, suggesting that if the immune mediated pathogenesis of HCC could be modulated, so could disease outcome.

Different strains of probiotic bacteria are known to mildly promote or suppress immune responses in the gut. In fact, selected strains of probiotic bacteria metabolize complex carbohydrates to short chain fatty acids (SCFAs), which are readily absorbed through the gut wall and activate regulatory T cells. A recent study showed that SCFAs ameliorated inflammation in a mouse model of colitis (Smith P M et al., Science, 2013; 341(6145):569-73). This may result from the fact that SCFAs, especially butyrate, may alter patterns of gene expression in target cells by inhibiting histone deacetylase activity (HDACi) (Tan J et al., Adv Immunol, 2014; 121:91-119). HBx has been shown to activate HDAC activity (Yoo et al., Oncogene, 2008; 27:3405-13), suggesting that the administration of selected probiotic bacteria or SCFAs made by these bacteria to HBx transgenic mice that develop HCC, may provide a simple and novel way to partially block the ability of HBx to promote tumor development.

There is a need in the art for effective therapy to prevent or delay the progression of liver inflammation into hepatocellular cancer. The present invention addresses this need.

SUMMARY OF THE INVENTION

The invention provides a method for preventing or delaying the onset of hepatocellular cancer in a subject. In one embodiment, the method comprises administering to the subject a therapeutically effective amount of a composition comprising at least one short chain fatty acid.

In one embodiment, the short chain fatty acid is selected from the group consisting of: formic acid, acetic acid, propionic acid, isobutyric acid, butyric acid, isovaleric acid, valeric acid, isocaproic acid, caproic acid, lactic acid, succinic acid, and pyruvic acid.

In one embodiment, the composition further comprises a pharmaceutically acceptable excipient.

In one embodiment, the composition is administered in combination with another therapeutic agent.

In one embodiment, the composition is administered orally.

In one embodiment, the composition is administered with food or drink.

The invention also provides a method for preventing or delaying the onset of hepatocellular cancer in a subject. In one embodiment, the method comprises administering to the subject a therapeutically effective amount of a composition comprising at least one probiotic bacteria.

In one embodiment, the probiotic bacteria is selected from the group consisting of: *Lactobacillus plantarum, Lactobacillus acidophilus, Lactobacillus paracasei, Leuconostoc mesenteroides, Lactobacillus bulgaricus, Lactobacillus sasei, Lactobacillus salivarius, Pediococcus pentosaceus, Streptococcus thermophiles, Bacillus subtilis, Bacillus coagulans, Enteroccous faecium, Bifidobacterium bifidum, Bifidobacterium lactis, Bifidobacterium longum,* and *Bifidobacterium infantis.*

In one embodiment, the composition further comprises a pharmaceutically acceptable excipient.

In one embodiment, the excipient comprises at least one prebiotic.

In one embodiment, the composition is administered in combination with another therapeutic agent.

In one embodiment, the composition s administered orally.

In one embodiment, the composition is administered with food or drink.

The invention also provides a kit for preventing or delaying the onset of hepatocellular cancer in a subject. In one embodiment, the kit comprises a composition comprising at least one short chain fatty acid.

The invention also provides a kit for preventing or delaying the onset of hepatocellular cancer in a subject. In one embodiment, the kit comprises a composition comprising at least one probiotic bacteria.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

In FIG. 5A, the number and size of observable tumors were then estimated on the surface of the liver lobules. Examples of these tumors are show on the livers of mice treated with PBS (FIGS. 5A and 5B) or with SCFAs (FIG. 5C) for 3 months starting at 9 months of age. Arrows are pointing to the tumor nodules. The results are representative of mice from each group. FIG. 5D is a summary of characteristics of tumors from both groups of mice.

FIG. 6A shows an example of a small tumor in SCFA treated mice (×40). FIG. 6B shows an example of a medium sized tumor nodule in an SCFA treated mouse (×40). FIG. 6C shows an example of a large tumor from PBS treated mouse. FIG. 6D shows a higher magnification of an HCC nodule from a PBS treated mouse (×100). Tumor (T) is on the left and non-tumor (NT) liver is on the right. Arrows are pointing to the tumor nodules. FIG. 6E shows the results of treatment of nine month old mice for three months with SCFAs (+) or PBS (−). Formalin fixed tissues were cut and stained by H & E. S=small tumors (<0.5 cm diameter); M=medium size tumors (0.5-1.0 cm diameter); L=large tumors (>1 cm).

FIG. 7 depicts a table showing the liver pathology in HBx mice treated with Synbiotic 2000™ from months 3-6.

FIG. 8 depicts a table showing the liver pathology in HBx mice treated with Synbiotic 2000™ from months 6-9.

FIG. 9 depicts a table showing the liver pathology in HBx mice treated with Synbiotic 2000™ from months 9-12.

FIG. 10 depicts a table showing the results of intrahepatic HBx staining in Synbiotic 2000™ treated and control mice.

DETAILED DESCRIPTION

Figures 1A, 1B, 1C:
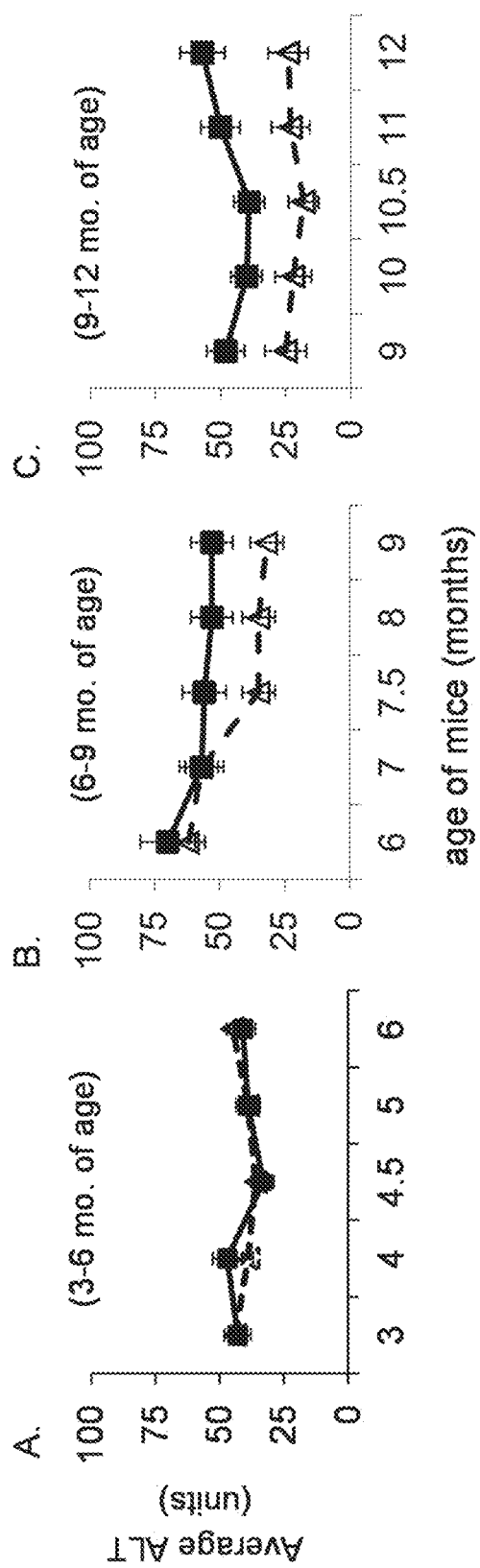
FIG. 1A-1C depicts graphs showing the alanine aminotransferase (ALT) values from mice treated with Synbiotic 2000™ (Δ) or PBS (■) at the indicated ages.

The present invention is partly based upon the discovery that short chain fatty acids are effective as a liver cancer chemopreventative therapeutic approach. The results presented herein demonstrate that the administration of short chain fatty acids to subjects having inflammation, hepatitis, and precancerous lesions in the liver is effective in preventing or delaying the progression of the liver disease into hepatocellular cancer.

Definitions

It is to be understood that the figures and descriptions of the present invention have been simplified to illustrate elements that are relevant for a clear understanding of the present invention, while eliminating, for the purpose of clarity, many other elements found in typical microscope devices. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, +1%, and ±0.1% from the specified value, as such variations are appropriate.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

A disease or disorder is "alleviated" if the severity of a sign or symptom of the disease or disorder, the frequency with which such a sign or symptom is experienced by a patient, or both, is reduced.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the compositions of the invention in prevention of the occurrence of tumor in the first place.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "inhibit," as used herein, means to suppress or block an activity or function by at least about ten percent relative to a control value. Preferably, the activity is suppressed or blocked by 50% compared to a control value, more preferably by 75%, and even more preferably by 95%.

The term "liver disease" includes diseases and conditions of the liver including liver cirrhosis, alcoholic and non-alcoholic fibrosis as well as to liver disease or changes associated with obesity, diabetes and metabolic syndrome. Other examples of liver diseases include: hepatitis, fatty liver, toxic liver failure, hepatic cirrhosis, diabetes-associated liver disease, liver steatosis, liver fibrosis, liver cirrhosis, chronic hepatitis and the like.

The term "probiotic organisms" includes live microorganisms that beneficially affect the health of a host. The benefits to the health of the host include, but are not limited to, improving the microbial balance of the intestines. Other beneficial effects to the host include, for example, enhancing the immune system, stimulation of phagocytic activity, stimulation of interferon, reduction of hypertension, decrease in the risk of cancer, increase in antimicrobial activity and immune-modulating effects, reduction of hypercholesterolemia, and treatment of cancer.

The terms "treatment", "treating" and the like are used herein to generally mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed to the disease. The term "treatment" as used herein covers any treatment of a disease in a subject and includes: (a) preventing a disease related to an undesired immune response from occurring in a subject which may be predisposed to the disease; (b) inhibiting the disease, i.e. arresting its development: or (c) relieving the disease, i.e. causing regression of the disease.

The terms "effective amount" and "pharmaceutically effective amount" refer to a sufficient amount of an agent to provide the desired biological result. That result can be reduction and/or alleviation of a sign, symptom, or cause of a disease or disorder, or any other desired alteration of a biological system. An appropriate effective amount in any individual case may be determined by one of ordinary skill in the art using routine experimentation.

A "therapeutically effective amount" refers to that amount which provides a therapeutic effect for a given condition and administration regimen. In particular, "therapeutically effective amount" means an amount that is effective to prevent, alleviate or ameliorate symptoms of the disease or prolong the survival of the subject being treated, which may be a human or non-human animal. Determination of a therapeutically effective amount is within the skill of the person skilled in the art.

As used herein, the term "pharmaceutical composition" refers to a mixture of at least one compound of the invention with other chemical components and entities, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to, intravenous, oral, aerosol, parenteral, ophthalmic, pulmonary and topical administration.

"Pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability, "Pharmaceutically acceptable carrier" refers to a medium that does not interfere with the effectiveness of the biological activity of the active ingredient(s) and is not toxic to the host to which it is administered.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pennsylvania), which is incorporated herein by reference.

The term "nutritional composition" may be a food product intended for human consumption, for example, a beverage, a drink, a bar, a snack, an ice cream, a dairy product, for example a chilled or a shelf-stable dairy product, a fermented dairy product, a drink, for example a milk-based drink, an infant formula, a growing-up milk, a confectionery product, a chocolate, a cereal product such as a breakfast cereal, a sauce, a soup, an instant drink, a frozen product intended for consumption after heating in a microwave or an oven, a ready-to-eat product, a fast food or a nutritional formula.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The phrase "biological sample" is used herein in its broadest sense. A sample may be of any biological tissue or fluid from which biomarkers of the present invention may be detected, extracted, isolated, characterized or measured. Examples of such samples include but are not limited to blood, lymph, urine, gynecological fluids, biopsies, amniotic fluid and smears. Samples that are liquid in nature are referred to herein as "bodily fluids." Biological samples may be obtained from a patient by a variety of techniques including, for example, by scraping or swabbing an area or by using a needle to aspirate bodily fluids. Methods for collecting various biological samples are well known in the art. Frequently, a sample will be a "clinical sample," i.e., a sample derived from a patient. Such samples include, but are not limited to, bodily fluids which may or may not contain cells, e.g., blood (e.g., whole blood, serum or plasma), urine, saliva, tissue or fine needle biopsy samples, and archival samples with known diagnosis, treatment and/or outcome history. Biological samples also include tissues, such as, frozen sections taken for histological purposes. The sample also encompasses any material derived by processing a biological sample. Derived materials include, but are not limited to, cells (or their progeny) isolated from the sample, proteins or nucleic acid molecules extracted from the sample. Processing of a biological sample may involve one or more of: filtration, distillation, extraction, concentration, inactivation of interfering components, addition of reagents, and the like.

As used herein, the term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating or preventing a disease in a subject.

"Instructional material," as that term is used herein, includes a publication, a recording, a diagram, or any other medium of expression which can be used to communicate the usefulness of components of the invention in the kit for identifying or alleviating or treating the various diseases or disorders recited herein. Optionally, or alternately, the instructional material may describe one or more methods of identifying or alleviating the diseases or disorders in a cell or a tissue of a subject. The instructional material of the kit may, for example, be affixed to a container that contains the compositions of the invention or be shipped together with a container that contains the compositions of the invention. Alternatively, the instructional material may be shipped separately from the container with the intention that the recipient uses the instructional material and the compound cooperatively.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments therebetween. This applies regardless of the breadth of the range.

Description

The present invention is partly based upon the discovery that introduction of probiotic bacteria that produce SCFAs, or introduction of the SCFAs alone, slows down the pathogenesis of HCC. The results presented herein demonstrate that SCFA producing probiotic bacteria, and corresponding SCFAs alone without probiotic treatment suppresses the appearance of dysplastic nodules and HCC in HBx transgenic mice. Therefore, the invention includes compositions and methods of using bacteria that produce SCFAs or introduction of the SCFAs alone as a simple approach for cancer chemoprevention. The present invention is a novel application towards liver cancer and other tumor types anatomically located distal from the large intestine.

Compositions

In one embodiment, the invention provides a short chain fatty acid or a combination of short chain fatty acids. In one embodiment, the invention provides a probiotic bacteria or a combination of probiotic bacteria. In various embodiments, the present invention includes compositions for preventing or delaying the onset of hepatocellular cancer in a subject, a cell, a tissue, or an organ in need thereof. The compositions of the invention include compositions for treating or preventing treating or preventing liver inflammation, liver disease, precancerous lesions, and the like.

Short Chain Fatty Acids

In various embodiments, the present invention includes compositions and methods of preventing or delaying the onset of hepatocellular cancer. In various embodiments, the present invention includes composition and methods of preventing or delaying the onset of hepatocellular cancer by treating or preventing treating or preventing liver inflammation, liver disease, and precancerous lesions. In one embodiment, the composition for preventing or delaying the onset of hepatocellular cancer comprises a short chain fatty acid or combination of short chain fatty acids.

In one embodiment, the invention provides a generic concept for administering short chain fatty acids as a therapy for preventing or delaying the onset of hepatocellular cancer. In one embodiment, the composition of the invention comprises a short chain fatty acid. In one embodiment, the short chain fatty acid is selected from the group including, but not limited to formic acid, acetic acid, propionic acid, isobutyric acid, butyric acid, isovaleric acid, valeric acid, isocaproic acid, caproic acid, lactic acid, succinic acid, pyruvic acid, octanoic acids, and dodecanoic acids. In one embodiment, a combination of short chain fatly acids comprises sodium acetate, sodium propionate, and sodium butyrate at equal amounts of at least 10 mM, at least 20 mM, at least 30 mM, 40 mM, 50 mM, 60 mM, 70 mM, 80 mM, 90 mM, 100 mM, or more.

Biologically active derivatives of short-chain fatty acids, e.g., having substituents on the carbon chain such as O, S, N, methyl, ethyl, halogen, and other groups that do not interfere with their biological activity may also be used to form the compositions of this invention.

Probiotic Bacteria

In various embodiments, the present invention includes compositions and methods of preventing or delaying the onset of hepatocellular cancer. In various embodiments, the present invention includes composition and methods of preventing or delaying the onset of hepatocellular cancer by treating or preventing treating or preventing liver inflammation, liver disease, and precancerous lesions. In one embodiment, the composition for preventing or delaying the onset of hepatocellular cancer comprises a probiotic bacteria or combination of probiotic bacteria.

In one embodiment, the invention provides a generic concept for administering probiotic bacteria as a therapy for preventing or delaying the onset of hepatocellular cancer. In one embodiment, the composition of the invention comprises a probiotic bacteria. In one embodiment, the probiotic bacteria is selected from the group including, but not limited to: *Lactobacillus plantarum, Lactobacillus acidophilus, Lactobacillus paracasei, Leuconostoc mesenteroides, Lactobacillus bulgaricus, Lactobacillus sasei, Lactobacillus salivarius, Pediococcus pentosaceus, Streptococcus thermophiles, Bacillus subtilis, Bacillus coagulants, Enteroccous faecium, Bifidobacterium bifidum, Bifidobacterium lactis, Bifidobacterium longum*, and *Bifidobacterium infantis*.

The probiotic bacteria of the present invention may also include mutant, variant, and genetically modified mutants of probiotic bacteria strains whose genetic and/or phenotypic properties are altered compared to the parent strain. Naturally occurring variants of probiotic bacteria strains include the spontaneous alterations of targeted properties selectively isolated while deliberate alteration of parent strain properties is accomplished by conventional genetic manipulation technologies, such as gene disruption, conjugative transfer, etc.

The general slate of probiotic bacteria is in the form of viable cells, or freeze-dried cells (which was used to generate the data herein). However, it can also be extended to non-viable cells such as killed cultures or compositions containing beneficial factors expressed by the probiotic bacteria. This could include thermally killed micro-organisms or micro-organisms killed by exposure to altered pH or subjection to pressure. With non-viable cells product preparation is simpler, cells may be incorporated easily into pharmaceuticals and storage requirements are much less limited than viable cells.

In one embodiment, the following composition and dosages of bacteria were used to generate the preliminary data presented herein: $10^{10}$ *Lactobacillus plantarum* 2362, $10^{10}$ *Lactobacillus paracasei* subsp *paracasei* 19, $10^{10}$ *Leuconostoc mesenteroids* 32-77; 1e, and $10^{10}$ *Pediococcus pentosaceus* 5-33:3 with a mixture of bioactive vegetable fiber types 2.5 g inulin, 2.5 g pectin, 2.5 g beta-glucan, and 2.5 g resistant starch (Synbiotic 2000™. Composition and dosages were administered daily for a period of three months.

Treatment Methods

In one embodiment, the present invention provides methods for treatment, inhibition, prevention, or reduction of hepatocellular cancer using a probiotic or combination of probiotics. In another embodiment, the present invention provides methods for treatment, inhibition, prevention, or reduction of hepatocellular cancer using a short chain fatty acid or combination or short chain fatly acids.

The present invention provides methods of preventing or inhibiting the onset of hepatocellular cancer. Inflammation of the liver, such as hepatitis, causes the initial lesions that result in hepatocellular damage, regeneration, and progression into precancerous and hepatocellular cancer nodules. Treating liver inflammation and other precancerous lesions can prevent or delay the onset of hepatocellular cancer. Methods for detecting liver disease and inflammation will be apparent to the skilled person and/or described herein.

The general approach to decreasing liver inflammation according to the present invention is to provide a cell with a short chain fatty acid. In one embodiment, the short chain fatty acid may be delivered directly. In another embodiment, the short chain fatty acid may be delivered indirectly through the metabolizing of complex carbohydrates (probiotics) by probiotic bacteria.

In order to effect inhibition of liver inflammation, the short chain fatty acids must be delivered into a cell. One mechanism for delivery is by any of the methods mentioned above which physically or chemically permeabilize the cell membrane. Another embodiment of the invention for transferring short chain fatty acids into cells may involve particle bombardment. This method depends on the ability to accelerate microprojectiles carrying the short chain fatty acids to a high velocity allowing them to pierce cell membranes and enter cells without killing them. Several devices for accelerating small particles have been developed. One such device relies on a high voltage discharge to generate an electrical current, which in turn provides the motive force. The microprojectiles used have consisted of biologically inert substances such as tungsten or gold beads.

In a further embodiment of the invention, the short chain fatty acids may be entrapped in a liposome. Liposomes are vesicular structures characterized by a phospholipid bilayer membrane and an inner aqueous medium. Multi-lamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers.

The compositions of the present invention and the pharmaceutical compositions containing said compounds, may be administered orally, and thus be formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. If formulated in form of a capsule, the compositions of the present invention comprise, in addition to the active compound and the inert carrier or diluent, a hard gelating capsule.

The compositions of the present invention and the pharmaceutical compositions containing said compounds may be further administered intranasally, i.e. by inhalation and thus may be formulated in a form suitable for intranasal administration, i.e. as an aerosol or a liquid preparation.

The compositions of the present invention may also, for example, be formulated as suppositories, containing conventional suppository bases for use in human or veterinary medicine or as pessaries, for example, containing conventional pessary bases.

One aspect of the invention provides a method of treating or preventing liver inflammation, liver diseases, and precancerous lesions using a composition of the invention. In one embodiment, the composition of the invention can be used to suppress the onset of hepatocellular cancer by treating or preventing liver inflammation, liver diseases, and precancerous lesions.

The following are non-limiting examples of liver diseases that can be treated by the disclosed methods and compositions: liver fibrosis, a liver disease associated with obesity, a liver disease associated with metabolic syndrome, liver cirrhosis, alcoholic cirrhosis, non-alcoholic cirrhosis, fatty liver, hepatic cirrhosis associated with diabetes, genetic liver diseases, liver steatosis, or chronic hepatitis. This includes chronic liver disease associated with other viruses, such as HIV, where an estimated 40% of individuals on long-term anti-retroviral therapy develop chronic liver disease.

In addition to hepatocellular cancer, the cancer that may be treated or immunized against (i.e., prophylactic treatment) by administration to a subject the composition of the invention can be a cancer selected from the group consisting of B cell lymphoma, T cell lymphoma, myeloma, leukemia, hematopoietic neoplasias, thymoma, lymphoma, sarcoma, lung cancer, non-Hodgkins lymphoma, Hodgkins lymphoma, uterine cancer, adenocarcinoma, breast cancer, pancreatic cancer, lung cancer, renal cancer, bladder cancer, prostate cancer, ovarian cancer, primary or metastatic melanoma, squamous cell carcinoma, basal cell carcinoma, brain cancer, angiosarcoma, hemangiosarcoma, head and neck carcinoma, thyroid carcinoma, soft tissue sarcoma, bone sarcoma, testicular cancer, uterine cancer, cervical cancer, gastrointestinal cancer, and any other cancer now known or later identified (see, e.g., Rosenberg (1996) Ann. Rev. Med. 47:481-491, the entire contents of which are incorporated by reference herein). Further immunogens contemplated within the scope of the present invention are infectious agent immunogens that can include any immunogen suitable for protecting a subject against an infectious disease, including but not limited to microbial, bacterial, protozoal, parasitic, fungal and viral diseases. In addition to inflammation associated cancers, SCFAs may also be useful in the treatment of inflammation associated autoimmune or autoaggressive diseases (e.g. rheumatoid arthritis).

In some embodiments of the methods for inhibiting cancer in an individual in need thereof, a second agent is administered to the individual, such as an antineoplastic agent. In some embodiments, the second agent comprises a second metastasis-inhibiting agent, such as a plasminogen antagonist, or an adenosine deaminase antagonist. In other embodiments, the second agent is an angiogenesis inhibiting agent.

The compositions of the invention can be used to prevent, abate, minimize, control, and/or lessen tumor metastasis in humans and animals. The disclosed compounds can also be used to slow the rate of primary tumor growth. The disclosed compounds when administered to a subject in need of treatment can be used to stop the spread of cancer cells. As such, the compounds disclosed herein can be administered as part of a combination therapy with one or more drugs or other pharmaceutical agents. When used as part of the combination therapy, the decrease in metastasis and reduction in primary tumor growth afforded by the disclosed compounds allows for a more effective and efficient use of any pharmaceutical or drug therapy being used to treat the patient. In addition, control of metastasis by the disclosed compound affords the subject a greater ability to concentrate the disease in one location.

The following are non-limiting examples of cancers that can be treated by the disclosed methods and compositions: Acute Lymphoblastic; Acute Myeloid Leukemia; Adrenocortical Carcinoma; Adrenocortical Carcinoma, Childhood; Appendix Cancer; Basal Cell Carcinoma; Bile Duct Cancer, Extrahepatic; Bladder Cancer; Bone Cancer; Osteosarcoma and Malignant Fibrous Histiocytoma; Brain Stem Glioma, Childhood; Brain Tumor, Adult; Brain Tumor, Brain Stem Glioma, Childhood; Brain Tumor, Central Nervous System Atypical Teratoid/Rhabdoid Tumor, Childhood; Central Nervous System Embryonal Tumors; Cerebellar Astrocytoma; Cerebral Astrocytotna/Malignant Glioma; Craniopharyngioma; Ependymoblastoma; Ependymoma; Medulloblastoma; Medulloepithelioma; Pineal Parenchymal Tumors of intermediate Differentiation; Supratentorial Primitive Neuroectodermal Tumors and Pineoblastoma; Visual Pathway and Hypothalamic Glioma; Brain and Spinal Cord Tumors; Breast Cancer; Bronchial Tumors; Burkitt Lymphoma; Carcinoid Tumor; Carcinoid Tumor, Gastrointestinal; Central Nervous System Atypical Teratoid/Rhabdoid Tumor; Central Nervous System Embryonal Tumors; Central Nervous System Lymphoma; Cerebellar Astrocytoma Cerebral Astrocytoma/Malignant Glioma, Childhood; Cervical Cancer; Chordoma, Childhood; Chronic Lymphocytic Leukemia; Chronic Myelogenous Leukemia; Chronic Myeloproliferative Disorders; Colon Cancer; Colorectal Cancer; Craniopharyngioma; Cutaneous T-Cell Lymphoma; Esophageal Cancer; Ewing Family of Tumors; Extragonadal Germ Cell Tumor; Extrahepatic Bile Duct Cancer; Eye Cancer, intraocular Melanoma; Eye Cancer, Retinoblastoma; Gallbladder Cancer; Gastric (Stomach) Cancer; Gastrointestinal Carcinoid Tumor; Gastrointestinal Stromal Tumor (GIST); Germ Cell Tumor, Extracranial; Germ Cell Tumor, Extragonadal; Germ Cell Tumor, Ovarian; Gestational Trophoblastic Tumor; Glioma; Glioma, Childhood Brain Stem; Glioma, Childhood Cerebral Astrocytoma; Glioma, Childhood Visual Pathway and Hypothalamic; Hairy Cell Leukemia; Head and Neck Cancer; Hepatocellular (Liver) Cancer; Histiocytosis, Langerhans Cell; Hodgkin Lymphoma; Hypopharyngeal Cancer; Hypothalamic and Visual Pathway Glioma; intraocular Melanoma; Islet Cell Tumors; Kidney (Renal Cell) Cancer; Langerhans Cell Histocytosis; Laryngeal Cancer; Leukemia, Acute Lymphoblastic; Leukemia, Acute Myeloid; Leukemia, Chronic Lymphocytic; Leukemia, Chronic Myelogenous; Leukemia, Hairy Cell; Lip and Oral Cavity Cancer; Liver Cancer; Lung Cancer, Non-Small Cell; Lung Cancer, Small Cell; Lymphoma, AIDS-Related; Lymphoma, Burkitt; Lymphoma, Cutaneous T-Cell; Lymphoma, Hodgkin; Lymphoma, Non-Hodgkin; Lymphoma, Primary Central Nervous System; Macroglobulinemia, Waldenstrom; Malignant Fibrous Histiocytoma of Bone and Osteosarcoma; Medulloblastoma; Melanoma; Melanoma, intraocular (Eye); Merkel Cell Carcinoma; Mesothelioma; Metastatic Squamous Neck Cancer with Occult Primary; Mouth Cancer; Multiple Endocrine Neoplasia Syndrome, (Childhood); Multiple Myeloma/Plasma Cell Neoplasm; Mycosis; Fungoides; Myelodysplastic Syndromes; Myelodysplastic Myeloproliferative Diseases; Myelogenous Leukemia, Chronic; Myeloid Leukemia, Adult Acute; Myeloid Leukemia, Childhood Acute; Myeloma, Multiple; Myeloproliferative Disorders, Chronic; Nasal Cavity and Paranasal Sinus Cancer; Nasopharyngeal Cancer; Neuroblastoma; Non-Small Cell Lung Cancer; Oral Cancer; Oral Cavity Cancer; Oropharyngeal Cancer; Osteosarcoma and Malignant Fibrous Histiocytoma of Bone; Ovarian Cancer; Ovarian Epithelial Cancer; Ovarian Germ Cell Tumor, Ovarian Low Malignant Potential Tumor; Pancreatic Cancer; Pancreatic Cancer, Islet Cell Tumors; Papillomatosis; Parathyroid Cancer; Penile Cancer; Pharyngeal Cancer; Pheochromocytoma; Pineal Parenchymal Tumors of Intermediate Differentiation; Pineoblastoma and Supratentorial Primitive Neuroectodermal Tumors; Pituitary Tumor; Plasma Celt Neoplasm/Multiple Myeloma; Pleuropulmonary Blastoma; Primary Central Nervous System Lymphoma; Prostate Cancer; Rectal Cancer; Renal Cell (Kidney) Cancer; Renal Pelvis and Ureter, Transitional Cell Cancer; Respiratory Tract Carcinoma Involving the NUT Gene on Chromosome 15; Retinoblastoma; Rhabdomyosarcoma; Salivary Gland Cancer; Sarcoma, Ewing Family of Tumors; Sarcoma, Kaposi; Sarcoma, Soft Tissue; Sarcoma, Uterine; Sezary Syndrome; Skin Cancer (Nonmelanoma); Skin Cancer (Melanoma); Skin Carcinoma, Merkel Cell; Small Cell Lung Cancer; Small Intestine Cancer; Soft Tissue Sarcoma; Squamous Cell Carcinoma, Squamous Neck Cancer with Occult Primary, Metastatic; Stomach (Gastric) Cancer; Supratentorial Primitive Neuroectodermal Tumors; T-Cell Lymphoma, Cutaneous; Testicular Cancer; Throat Cancer; Thymoma and Thymic Carcinoma; Thyroid Cancer; Transitional Cell Cancer of the Renal Pelvis and Ureter; Trophoblastic Tumor, Gestational; Urethral Cancer; Uterine Cancer, Endometrial; Uterine Sarcoma; Vaginal Cancer; Vulvar Cancer; Waldenstrom Macroglobulinemia; and Wilms Tumor.

In one embodiment, the invention provides a method to treat cancer comprising treating the subject prior to, concurrently with, or subsequently to the treatment with a composition of the invention, with a complementary therapy for the cancer, such as surgery, chemotherapy, chemotherapeutic agent, radiation therapy, or hormonal therapy or a combination thereof.

In another embodiment, the invention provides a method to treat cancer comprising treating the subject prior to, concurrently with, or subsequently to the treatment with a composition of the invention, with a complementary therapy for the cancer, such as surgery, chemotherapy, chemotherapeutic agent, radiation therapy, or hormonal therapy or a combination thereof.

Chemotherapeutic agents include cytotoxic agents (e.g., 5-fluorouracil, cisplatin, carboplatin, methotrexate, daunorubicin, doxorubicin, vincristine, vinblastine, oxorubicin, carmustine (BCNU), lomustine (CCNU), cytarabine USP, cyclophosphamide, estramucine phosphate sodium, altretamine, hydroxyurea, ifosfamide, procarbazine, mitomycin, busulfan, cyclophosphamide, mitoxantrone, carboplatin, cisplatin, interferon alfa-2a recombinant, paclitaxel, teniposide, and streptozoci), cytotoxic alkylating agents (e.g., busulfan, chlorambucil, cyclophosphamide, melphalan, or ethylesulfonic acid), alkylating agents (e.g., asaley, AZQ, BCNU, busulfan, bisulphan, carboxyphthalatoplatinum, CBDCA, CCNU, CHIP, chlorambucil, chlorozotocin, cisplatinum, clomesone, cyanomorpholinodoxorubicin, cyclodisone, cyclophosphamide, dianhydrogalactitol, fluorodopan, hepsulfam, hycanthone, iphosphamide, melphalan, methyl CCNU, mitomycin C, mitozolamide, nitrogen mustard, PCNU, piperazine, piperazinedione, pipobroman, porfiromycin, spirohydantoin mustard, streptozotocin, teroxirone, tetraplatin, thiotepa, triethylenemelamine, uracil nitrogen mustard, and Yoshi-864), antimitotic agents (e.g., allocolchicine, Halichondrin M, colchicine, colchicine derivatives, dolastatin 10, maytansine, rhizoxin, paclitaxel derivatives, paclitaxel, thiocolchicine, trityl cysteine, vinblastine sulfate, and vincristine sulfate), plant alkaloids (e.g., actinomycin D, bleomycin, L-asparaginase, idarubicin, vinblastine sulfate, vincristine sulfate, mitramycin, mitomycin, daunorubicin, VP-16-213, VM-26, navelbine and taxotere), biologicals (e.g., alpha interferon, BCG, G-CSF, GM-CSF, and interleukin-2), topoisomerase I inhibitors (e.g., camptothecin, camptothecin derivatives, and morpholinodoxorubicin), topoisomerase II inhibitors (e.g., mitoxantron, amonafide, m-AMSA, anthrapyrazole derivatives, pyrazoloacridine, bisantrene HCL, daunorubicin, deoxydoxorubicin, menogaril, N,N-dibenzyl daunomycin, oxanthrazole, rubidazone, VM-26 and VP-16), and synthetics (e.g., hydroxyurea, procarbazine, o,p'-DDD, dacarbazine, CCNU, BCNU, cis-diamminedichloroplatimun, mitoxantrone, CBDCA, levamisole, hexamethylmelamine, all-trans retinoic acid, gliadel and porfimer sodium).

Antiproliferative agents are compounds that decrease the proliferation of cells. Antiproliferative agents include alkylating agents, antimetabolites, enzymes, biological response modifiers, miscellaneous agents, hormones and antagonists, androgen inhibitors (e.g., flutamide and leuprolide acetate), antiestrogens (e.g., tamoxifen citrate and analogs thereof, toremifene, droloxifene and roloxifene), Additional examples of specific antiproliferative agents include, but are not limited to levamisole, gallium nitrate, granisetron, sargramostim strontium-89 chloride, filgrastim, pilocarpine, dexrazoxane, and ondansetron.

The compositions of the invention can be administered alone or in combination with other anti-tumor agents, including cytotoxic/antineoplastic agents and anti-angiogenic agents. Cytotoxic/anti-neoplastic agents are defined as agents which attack and kill cancer cells. Some cytotoxic/anti-neoplastic agents are alkylating agents, which alkylate the genetic material in tumor cells, e.g., cis-platin, cyclophosphamide, nitrogen mustard, trimethylene thiophosphoramide, carmustine, busulfan, chlorambucil, belustine, uracil mustard, chlomaphazin, and dacabazine. Other cytotoxic/anti-neoplastic agents are antimetabolites for tumor cells, e.g., cytosine arabinoside, fluorouracil, methotrexate, mercaptopurine, azathioprime, and procarbazine. Other cytotoxic/anti-neoplastic agents are antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/anti-neoplastic agents are mitotic inhibitors (vinca alkaloids). These include vincristine, vinblastine and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

Anti-angiogenic agents are well known to those of skill in the art. Suitable anti-angiogenic agents for use in the methods and compositions of the present disclosure include anti-VEGF antibodies, including humanized and chimeric antibodies, anti-VEGF aptamers and antisense oligonucleotides. Other known inhibitors of angiogenesis include angiostatin, endostatin, interferons, interleukin 1 (including alpha and beta) interleukin 12, retinoic acid, and tissue inhibitors of metalloproteinase-1 and -2. (TIMP-1 and -2). Small molecules, including topoisomerases such as razoxane, a topoisomerase II inhibitor with anti-angiogenic activity, can also be used.

Other anti-cancer agents that can be used in combination with the disclosed compounds include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarahine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxy vitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene;

emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitahine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein, sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide, tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine, triciribine; trimetrexate; triptorelin; tropisetron, turosteride; tyrosine kinase inhibitors, tyrphostins; UBC inhibitors; ubenimex; urogenital sinus-derived growth inhibitory factor; urokinase receptor antagonists; vapreotide; variolin B; vector system, erthrocyte gene therapy; velaresol; veramine; verdins; verteporfin; vinorelbine; vinxaltine, vitaxin; vorozole; zanoterone, zeniplatin; zilascorb; and zinostatin stimalamer. In one embodiment, the anti-cancer drug is 5-fluorouracil, taxol, or leucovorin.

Pharmaceutical Compositions

The present invention includes pharmaceutical compositions comprising one or more compositions of the present invention. The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Said compositions may comprise additional medicinal agents, pharmaceutical agents, carriers, buffers, adjuvants, dispersing agents, diluents, and the like depending on the intended use and application.

Examples of suitable pharmaceutical carriers, excipients and/or diluents are well known in the art and include, but are not limited to, a gum, a starch (e.g. corn starch, pre-gelatinized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

Pharmaceutically acceptable carriers for liquid formulations are aqueous or non-aqueous solutions, suspensions, emulsions or oils, Examples of non-aqueous solvents are propylene glycol, polyethylene glycol, and injectable organic esters such as ethyl oleate. Examples of oils are those of animal, vegetable, or synthetic origin, for example, peanut oil, soybean oil, olive oil, sunflower oil, turmeric oil, fish-liver oil, another marine oil, or a lipid from milk or eggs.

Aqueous carriers include water, alcoholic/aqueous solutions, emulsions or suspensions, including saline and buffered media such as phosphate buffered saline solutions, water, emulsions, such as oil/water emulsions, various types of wetting agents, sterile solutions etc. Compositions comprising such carriers can be formulated by well-known conventional methods. Suitable carriers may comprise any material which, when combined with the biologically active compound of the invention, retains the biological activity. Preparations for parenteral administration may include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles may include sodium chloride solution, Ringer's dextrose, dextrose and sodium chloride, lactated Ringer's, or fixed oils. Intravenous vehicles may include fluid and nutrient replenishes, electrolyte replenishers (such as those based on Ringer's dextrose), and the like. Preservatives and other additives may also be present including, for example, antimicrobials, anti-oxidants, chelating agents, and inert gases and the like, in addition, the pharmaceutical composition of the present invention might comprise proteinaceous carriers, like, e.g., serum albumin or immunoglobulin, preferably of human origin.

The pharmaceutical compositions provided herein may also be administered as controlled-release compositions, i.e. compositions in which the active ingredient is released over a period of time after administration. Controlled- or sustained-release compositions include formulation in lipophilic depots (e.g. fatty acids, waxes, oils). In another embodiment, the composition is an immediate-release composition, i.e. a composition in which all the active ingredient is released immediately after administration.

Further, the pharmaceutical compositions according to the invention and as described herein in the various embodiments may or a composition comprising said compound may be administered admixed to food, functional food, drinks, medicinal food.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions that are useful in the methods of the invention may be prepared, packaged, or sold in formulations suitable for ophthalmic, oral, rectal, vaginal, parenteral, topical, pulmonary, intranasal, buccal, intratumoral, epidural, intracerebral, intracerebroventricular, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

Compositions of the present invention may also comprise a prebiotic component, "Prebiotic" includes substances or compounds that are fermented by the intestinal flora of the pet and hence promote the growth or development of lactic acid bacteria in the gastro-intestinal tract of the pet at the expense of pathogenic bacteria. The result of this fermentation can be a release of fatty acids, in particular short-chain fatty acids in the colon. This release can have the effect of reducing the pH value in the colon. Non-limiting examples of suitable prebiotics include oligosaccharides, such as inulin and its hydrolysis products commonly known as fructooligosaccharides, galacto-oligosaccharides, xylo-oligosaccharides, or oligo derivatives of starch (such as pectin, beta-glucan, and resistant starch). The prebiotics may be provided in any suitable form. For example, the prebiotic may be provided in the form of plant material that contains the fiber. Suitable plant materials include asparagus, artichokes, onions, wheat or chicory, or residues of these plant materials. Alternatively, the prebiotic fiber may be provided as an inulin extract, for example extracts from chicory are suitable. Suitable inulin extracts may be obtained from Orafti SA of Tidemont 3300, Belgium under the trade mark "Raftiline". For example, the inulin may be provided in the form of Raftiline (g) ST which is a fine white powder, which contains about 90 to about 94% by weight of inulin, up to about 4% by weight of glucose and fructose, and about 4 to 9% by weight of sucrose. Alternatively, the fiber may be in the form of a fructooligosaccharide such as obtained from Orafti SA of Tirlemont 3300, Belgium under the trade mark "Raftilose". For example, the inulin may be provided in the form of Raftilose (g) P95. Otherwise, the fructooligosaccharides may be obtained by hydrolyzing inulin, by enzymatic methods, or by using micro-organisms.

Pharmaceutical compositions also include nutritional compositions, such as oral nutritional compositions for oral consumption and optionally for enteral adsorption, wherein the nutritional composition includes the compounds of the present invention.

If the nutritional compositions are formulated to be administered orally, the compositions may be a liquid oral nutritional supplement (e.g., incomplete feeding) or a complete feeding. In this manner, the nutritional compositions may be administered in any known form including, for example, tablets, capsules, liquids, chewables, soft gels, sachets, powders, syrups, liquid suspensions, emulsions and solutions in convenient dosage forms.

A nutritional formula encompasses any nutritionally complete or supplementary formulation (a nutritional supplement, for example). As used herein, "nutritionally complete" are preferably nutritional products that contain sufficient types and levels of macronutrients (protein, fats and carbohydrates) and micronutrients to be sufficient to be a sole source of nutrition for the subject to which it is being administered to. Patients can receive 100% of their nutritional requirements from such complete nutritional compositions. According to one embodiment, the nutritional formula is a supplementary formulation providing supplementary nutrition. A "supplementary formula" may not be nutritionally complete, but preferably contains specific nutrients that are supportive, for example in combination with physical exercise, with further of the beneficial effects of the invention, and/or which address specific or additional needs of the subject.

The nutritional formula may be a generally applicable nutritional formula, for example adapted to subjects of a specific age, for example a formula for children, but it may also be a formula for elderly patients, for intensive care patients, or a specially adapted formula for patients suffering from a specific disease, for example. Any nutritional formula may be reconstitutable, that is, present in a substantially dried, for example powdered form, or ready-to-drink, in the form of liquid formulas, for example.

Kits of the Invention

The invention also includes a kit comprising compounds useful within the methods of the invention and an instructional material that describes, for instance, the method of administering short chain fatty acids as described elsewhere herein, or the method of administering probiotic bacteria as described elsewhere herein. Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally acceptable diluent or solvent, such as water or 1,3 butane diol, for example. Other acceptable diluents and solvents include, but are not limited to, Ringer's solution, isotonic sodium chloride solution, and fixed oils such as synthetic mono or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1

Symbiotic Bacteria Provide Chemoprevention Against Hepatitis B Virus Mediated Hepatocellular Carcinoma in Hepatitis Bx Transgenic Mice Chronic infection with hepatitis B virus (HBV) is associated with the development of progression of chronic liver disease (CLD) and the appearance of hepatocellular carcinoma (HCC). HCC is a prevalent cancer worldwide with few treatment options. Given that HCC develops decades after infection, and appears most often on the background of chronic inflammation, experiments were designed to test the hypothesis that selected probiotic bacteria that are known to suppress inflammation could be used as a simple and inexpensive means to prevent or delay the appearance of HCC. To test this, hepatitis Bx (HBx) transgenic mice, which develop progressive liver lesions that culminate in HCC, were treated with a mixture of probiotic bacteria (Synbiotic 2000™). The result showed a significant reduction in the number and size of dysplastic and HCC nodules compared to control transgenic mice. Microarray analysis of selected immune and cancer associated markers showed a strong reduced expression in the liver of mice treated with Synbiotic 2000™ compared to control mice. Since the bacteria used metabolize complex carbohydrates to short chain fatty acids (SCFAs), which are known to have anti-inflammatory properties in other systems, HBx transgenic mice were fed a combination of SCFAs made by Synbiotic 2000™ (acetate, proprionate, butyrate) in the absence of bacteria in a parallel experiment. The results again showed a strong reduction in the number and size of dysplastic and HCC nodules. These results show that Synbiotic 2000™ or their metabolic byproducts in the form of SCFAs attenuate the pathogenesis of HCC, and may be useful as a cancer chemopreventative approach, not only for HCC, but perhaps against other cancers that often develop on the background of chronic inflammation.

The materials and methods used in these experiments are now described.

Materials and Methods

Mice

In order to study the pathogenesis of HCC, and to evaluate new treatment approaches, an HBx transgenic mouse model has been created (Yu D Y et al., J Hepatol, 1999; 31:123-132'). At birth, these HBx transgenic mice have little or no HBx expression and no pathology in the liver. By 3-4 months of age, they develop detectable HBx associated with hepatitis/steatosis. By 6-7 months of age, the presence, frequency and distribution of intrahepatic HBx is much higher, and this is associated with the appearance of dysplastic nodules and microscopic HCC. By 9-10 months of ague, extensive HBx staining is associated with the appearance of macroscopic HCC nodules. Given that this sequence of events is similar to that in chronic human infections, this animal model was used for the current work.

To test the hypothesis that Synbiotic 2000™ or their SCFA metabolic products will delay or prevent the pathogenesis of HBV associated HCC, an HBx transgenic mouse was used (Arzumanyan A et al., Cancer Res, 2012; 72(22):5912-5920). The transgenic mouse was made on a C57B16 background using the HBx gene along with its enhancer/promoter complex so that HBx was expressed only in differentiated hepatocytes. This resulted in an age dependent increase in HBx expression which was associated with the progression of lesions in the liver. These mice were supplied by Dr. Dr. Dae-Yeul Yu (Korea Research Institute of Bioscience and Biotechnology, Taejon, Korea) and mated with CBA mice. A colony of C57B16/CBA mice was then generated by brother-sister matings. The latter had a higher incidence of animals with progressive lesions compared to the original C57B16 transgenic mouse strain.

Probiotic Bacteria and Short Chain Fatty Acids (SCFAs)

Synbiotic 2000™ was provided by Medipharm (Des Moines, Iowa). It contains a mix of four lactic acid producing bacilli (1010 *Lactobacillus plantarum* 2362, 1010 *Lactobacillus paracasei* subsp *paracasei* 19, 1010 *Leuconostoc mesenteroides* 32-77:1e, and 1010 *Pediococcus pentosaceus* 5-33:3) and a mixture of four bioactive vegetable fiber types (2.5 g inulin; 2.5 g pectin; 2.5 g beta-glucan and 2.5 g resistant starch) per packet. It was administered daily by gavage at 0.05 g/dose (2.5 g/30 ml water, 0.6 ml dose/mouse) for a period of three months.

Short chain fatty acids, consisting of sodium acetate, sodium propionate, and sodium butyrate were purchased from Acros Organics (Geel, Belgium) through Fisher Scientific (Fairlawn, New Jersey). They were administered by gavage with 0.2 ml containing 150 mM of SCFAs (50 mM of each SCFA) per day for 30 days.

Protocol

HBx transgenic mice were tested for the presence of the HBx gene by tail snip analysis and real time PCR amplification. HBx protein was assessed by immunohistochemical staining of sections cut from formalin-fixed, paraffin embedded liver tissue, as previously described (Arzumanyan A et al., Cancer Res, 2012; 72(22):5912-5920). For this work, groups of 10 HBx transgenic mice at 3, 6 and 9 months were gavaged with freshly reconstituted Symbiotic 2000™ daily for 3 months. Control groups included age and gender matched HBx transgenic mice that were gavaged with PBS in place of Synbiotic 2000™. Groups of age and gender matched HBx negative littermates were gavaged with Synbiotic 2000™ or PBS. All mice were periodically bled retro-orbitally for alanine amino-transferase (ALT) determinations (ALT/GPT 50, Sigma Chemical Co., St. Louis, Missouri) and after three months of treatment, euthanized. Mice were weighed just prior to each bleeding, and liver weights were determined following euthanasia. Tumor nodules visible on the surface of each liver were enumerated. Samples of liver from each lobe were then embedded and sections stained by H & E. Slides from each liver were examined by light microscopy under code independently by two individuals, and the various lesions recorded. The remaining liver tissues from all mice were snap-frozen in liquid nitrogen and stored at −80° C. All animal protocols for this work were approved by the Temple University Institutional Animal Care and Use Committee.

RNA Isolation and cDNA Synthesis

Frozen liver tissue samples from all mice were homogenized in lysis buffer (RTL) using a handheld rotor-stator homogenizer with autoclaved non-disposable probes (TissueRuptor, Qiagen). Total RNA from each sample was then extracted using the RNeasy Mini Kit (Qiagen) following the manufacturer protocol. Contaminating DNA was removed using an RNase-Free DNase kit (Qiagen). RNA concentration was determined reading the absorbance of 1 μl of each sample at 260 and 280 nm in a Nanodrop UV-Vis Spectrophotometer (Thermo Scientific). A typical yield of 50 to 1800 ng/μl in a final volume of 50 μl elution buffer was obtained from an initial tissue sample of 30 mg. The samples were then aliquoted to a final concentration of 50 ηg/μl and stored at −80° C.

Reverse transcription used 500 ηg of total RNA from each of these samples and was achieved using the RT2 First Strand Kit (Qiagen) according to manufacturer's instructions provided. Samples were then stored at −20° C. until use in qPCR arrays.

qPCR Array Assay

A Custom RT2 Profiler PCR-array (SA Biosciences, Qiagen, Izasa), formatted in microwells, contained a panel of genes tailored to the specific research interests of this study. Amplification of cDNA was performed using RT2 SYBR Green Rox qPCR. Mastermix (Qiagen). Each reverse transcribed sample was diluted 1:3 and 51 μl of it was added to 550 μl mastermix. From this reaction mixture, 10 μl of each mix was loaded into each well.

Statistical Analysis

The Chi-square test was used to assess the relationships between the different liver lesions in treated compared to control mice. Significance was obtained when p<0.05. The Student's t test was used to assess the differences in tumor size between treated and control mice. Significance was obtained when P<0.05.

The results of the experiments are now described.

Effect of Synbiotic 2000™ Upon Chronic Liver Disease and HCC

Given that the pathogenesis of HCC is immune mediated (Feitelson M A et al., Cancer Lett. 2009; 286(1):69-79), and that the probiotic bacteria in Synbiotic 2000™ may have anti-inflammatory properties, experiments were designed to test the hypothesis that feeding HBx transgenic mice with Synbiotic 2000™ may retard or block the development of CLD and its progression to HCC. Accordingly, 10 mice per group starting at ages 3, 6 and 9 months were gavaged for 3 months. Mice were retro-orbitally bled just prior to the beginning of treatment, and at monthly intervals until the animals were euthanized. The livers were then removed, and samples from each lobe formalin-fixed and paraffin embedded, while the remaining liver samples were snap frozen.

Given that HBx transgenic mice develop hepatitis, serial serum samples were tested for ALT enzyme activity. The mean ALT values from most HBx mice treated with PBS were significantly higher than those of age and gender matched HBx mice treated with Synbiotic 2000™ in parallel (FIG. 1). Among mice 3-6 months of age, there was no difference in the mean ALT values (FIG. 1A), but among mice 6-9 months of age, the mean differences from 7.5-9 months were significantly different (t=14.18, P<0.001) (FIG. 1B), as were mean differences among mice treated from 9-12 months of age (t=6.78, P<0.001) (FIG. 1C). These findings suggest that the more severe and progressive the liver disease with age, the greater the difference in mean ALT values among Synbiotic 2000™ treated mice compared to controls. It should be stressed, however, that although the mean ALT values for Synbiotic 2000™ compared to PBS treated mice were statistically different in many of these cases, ALT elevations were mild and many of the differences were between values less than 60 units.

Figures 2A, 2B, 2C:
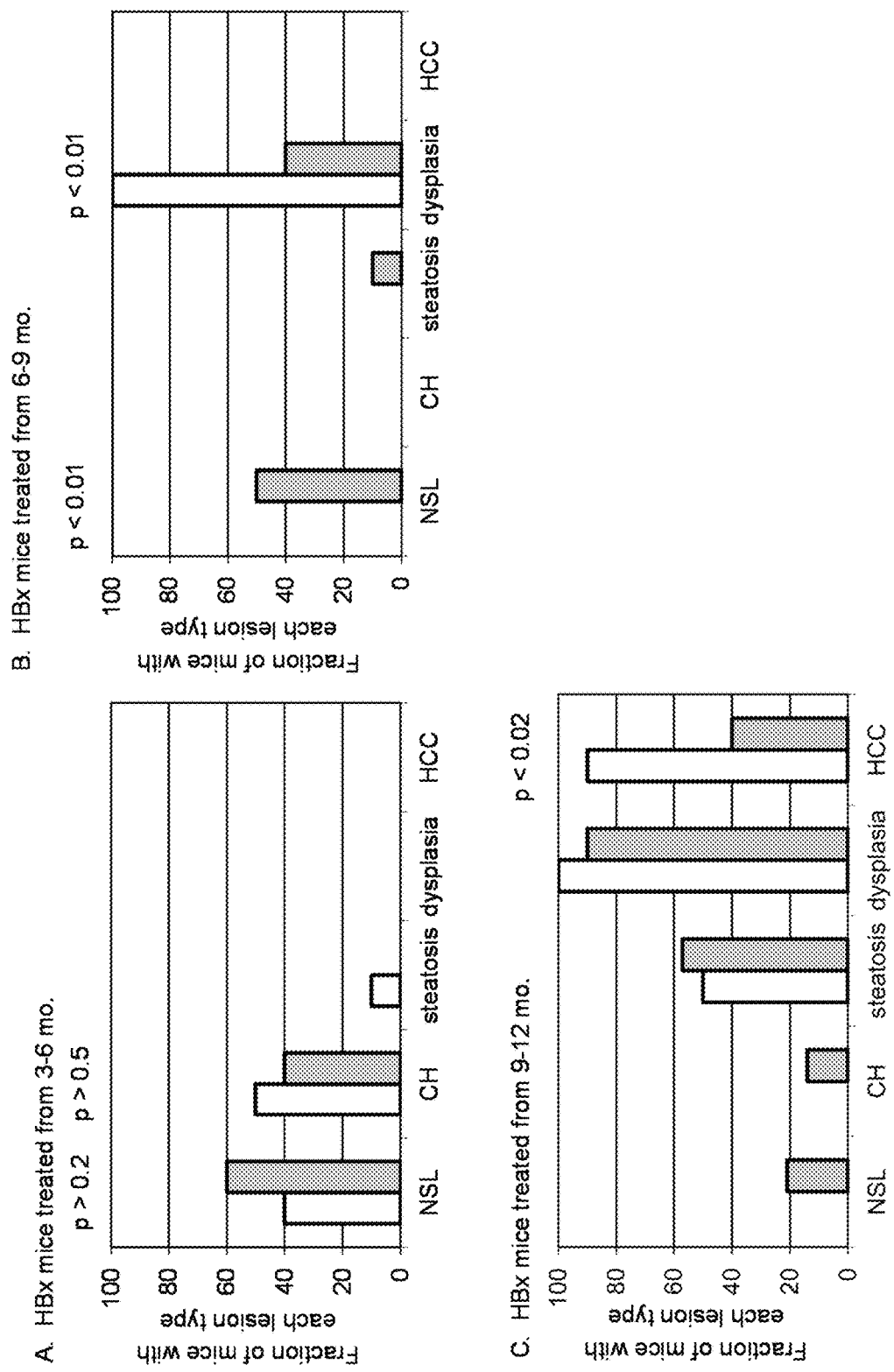
FIG. 2A-2C depicts graphs comparing the frequency of occurrence of different liver pathologies. This is shown in (FIG. 2A) for 3 month old mice evaluated at 6 months for evidence of steatosis and dysplasia, for (FIG. 2B) 6 month old mice evaluated at 9 months for evidence of dysplasic nodules and early HCC, and for (FIG. 2C) 9 month old mice evaluated at 12 months of age for evidence of large HCC nodules, Gray bars are test mice fed Synbiotic 2000™ for 3 months starting at the indicated ages. White bars are control mice fed PBS. HBx transgenic mice were made using the HBx enhancer/promoter regions just upstream of the X gene. This enhancer/promoter becomes active in mature hepatocytes, so that HBx is undetectable at birth but accumulates within hepatocytes with age (Yu D Y et al., J Hepatol, 1999; 31:123-432). From an immunological perspective, HBx is recognized as being foreign, which triggers inflammatory responses (hepatitis) and steatosis (fatty liver) by 4-5 months of age. This progresses into dysplasia (a preneoplastic lesion) by 6-7 months of age, dysplastic nodules and microscopic HCC by 9-10 months of age, and finally large HCC by 10-12 months of age.

The impact of Synbiotic 2000™ upon the progression of chronic liver disease and development of HCC was then evaluated in HBx mice treated for three months starting at 3, 6 or 9 months of age. Among 3 month old mice euthanized at 6 months of age, 5 out of 10 PBS treated mice (50%) had periportal hepatitis, while this was observed in 4 out of 10 Synbiotic 2000™ treated mice (FIG. 7). Although the trend was that the Symbiotic treated mice had fewer and generally milder lesions compared to PBS treated mice, these differences were not statistically significant (FIG. 2A). In contrast, among 6 month old mice, all 10 PBS controls had evidence of widespread dysplasia by the time their livers were evaluated at month 9, while among Synbiotic 2000™ treated mice, only 40% had evidence of dysplasia. In the Synbiotic 2000™ treated group, there was generally fewer dysplastic cells and nodules compared to control mice. Importantly, half the mice treated with Synbiotic 2000™ had histologically normal liver (FIG. 2B, FIG. 8). When a parallel experiment was conducted with 9 month old mice, 90% of PBS treated mice had HCC nodules, while only 40% of Synbiotic 2000™ treated mice had HCC (FIG. 2C). Many of these mice had multiple lesion types (e.g., hepatitis, dysplasia and/or HCC), and were characterized by multiple nodules of dysplastic cells and multi-nodular HCC (FIG. 9). As expected, HBx negative mice treated in parallel all showed no significant lesions in their livers (data not shown). Thus, treatment with Symbiotic bacteria appeared to produce a qualitative and quantitative change in the liver lesions present among mice of different ages.

To determine whether the observations above with Synbiotic 2000™ were associated with toxicity, all mice were weighted at the end of the experiment. Livers were also weighed. In all groups of mice, there was no statistical difference between body or liver weights between those treated with Synbiotic 2000™ compared to those treated with placebo. For example, among the nine month old group fed for three months, the mean body weight for the placebo treated mice was 45.3 grams while the mean weight of the Synbiotic 2000™ treated mice was 49.2 grams (t=0.879; P>0.3). The mean liver weights were 2.62 and 2.68 grams, respectively (t=0.102; P>0.9), Analogous results were observed in younger mice (data not shown). These results indicate that there is no overt toxicity associated with Synbiotic 2000™ treatment over a period of 3 months.

Prior work from this and other laboratories showed a direct correlation between intrahepatic HBx expression and the severity of chronic liver disease (Jin Y M et al., J Viral Hepat, 2001; 8(5):322-30; Feitelson M A et al., J Hepatol, 1993; 17 (Suppl. 3):S24-S34; Wang W et al., Hepatology, 1998; 14:29-37; Wang W et al., Cancer Res, 1991; 51:4971-4977). To test whether this occurs here, and is inversely related to Synbiotic 2000™ treatment, liver sections from each group of treated and control mice were evaluated for HBx expression by immunohistochemical staining. Among 3 month old mice, cytoplasmic HBx was weak to modest (+1 and +2) in scattered hepatocytes or groups of hepatocytes (FIG. 10). The presence, frequency and distribution of intrahepatic HBx increased in the livers of older animals (FIG. 10). When HBx mice were treated with Synbiotic 2000™, HBx staining decreased compared to control mice (FIG. 10, FIG. 3).

Partial Expression Profile of Selected Markers Associated with Tumorigenicity and Immunity Given that HCC arises in the context of chronic inflammation, and that HBx promotes the development of this tumor type, limited PCR array analysis was performed to determine whether Synbiotic 2000™ impacted upon the expression of selected tumor associated signaling pathways and/or cytokines that may contribute to the pathogenesis of HCC. When 3 month old mice were treated with Synbiotic 2000™ for 3 months, and the expression profiles of selected genes compared to that of PBS treated animals, markers associated with tumorigenesis were up-regulated 1.5-3 fold (FIG. 4A). When Synbiotic 2000™ treatment was administered to 6 month old mice for 3 months, expression of most tumor associated markers was neither up- nor down-regulated in test compared to control mice (FIG. 4B). A notable exception was EGFR, which stimulates growth, and was down-regulated with Synbiotic 2000™ by more than 8-fold. In contrast, when Synbiotic 2000™ was given to 9 month old mice for 3 months, most markers associated with tumorigenesis were strongly down-regulated in test compared to placebo treated animals (FIG. 4C). These markers included Gli1 and 2, which are signaling molecules in the hedgehog pathway, several Notch receptors. TGFβ-1 and 2 and TGFβR1 (which normally negatively regulate cell growth), Tcf3 (which is important to β-catenin signaling), Akt1 (which is often constitutively activated in carcinogenesis), as well as MMP-9 and -10 (which promote metastasis) (FIG. 4C). With regard to immune mediated markers in 3 month old mice that were euthanized at 6 months, most immune markers were neither elevated nor suppressed within 2-fold in test compared to placebo treated (FIG. 4A). Similar results were obtained in 6 month mice euthanized at 9 months (FIG. 4B). However, among 9 month old mice that were euthanized at 12 months, all of the immune response associated markers were depressed in test compared to control mice (FIG. 4C), suggesting a shift in the nature of the immune responses against HBx and/or HBx induced changes in the liver that accompany disease progression. When this analysis was performed on livers from age and gender matched transgene negative littermates, there were no statistically significant differences in the levels of these markers, suggesting that their differences were related to the increasing impact of HBx on the liver, and not due to age related changes (data not shown).

Treatment with Short Chain Fatty Acids (SCFAs)

Figures 5A, 5B, 5C, 5D:
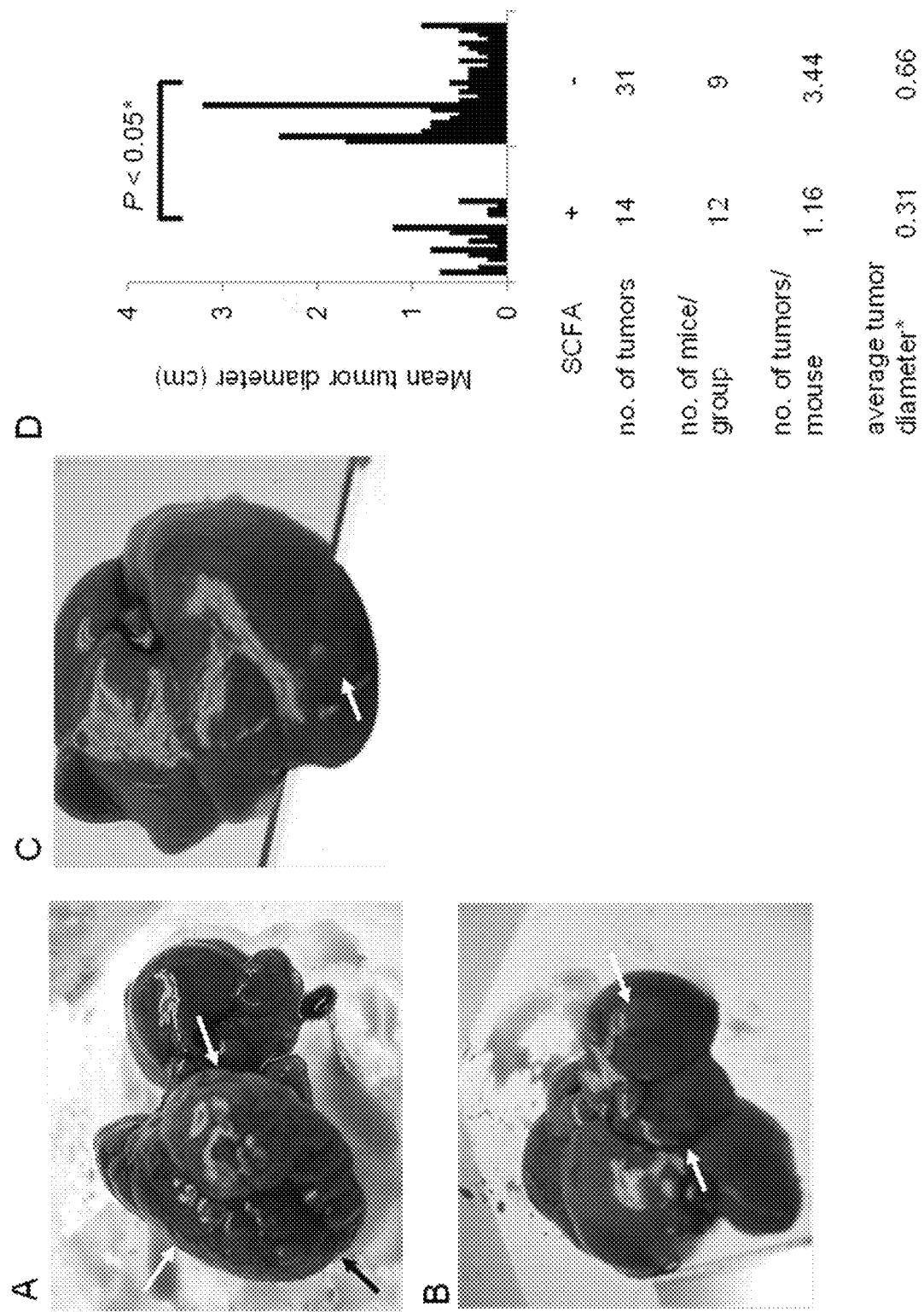
FIG. 5A-5D depicts livers from 4 SCFA fed mice obtained at 12 months of age.
Figures 6A, 6B, 6C, 6D, 6E:
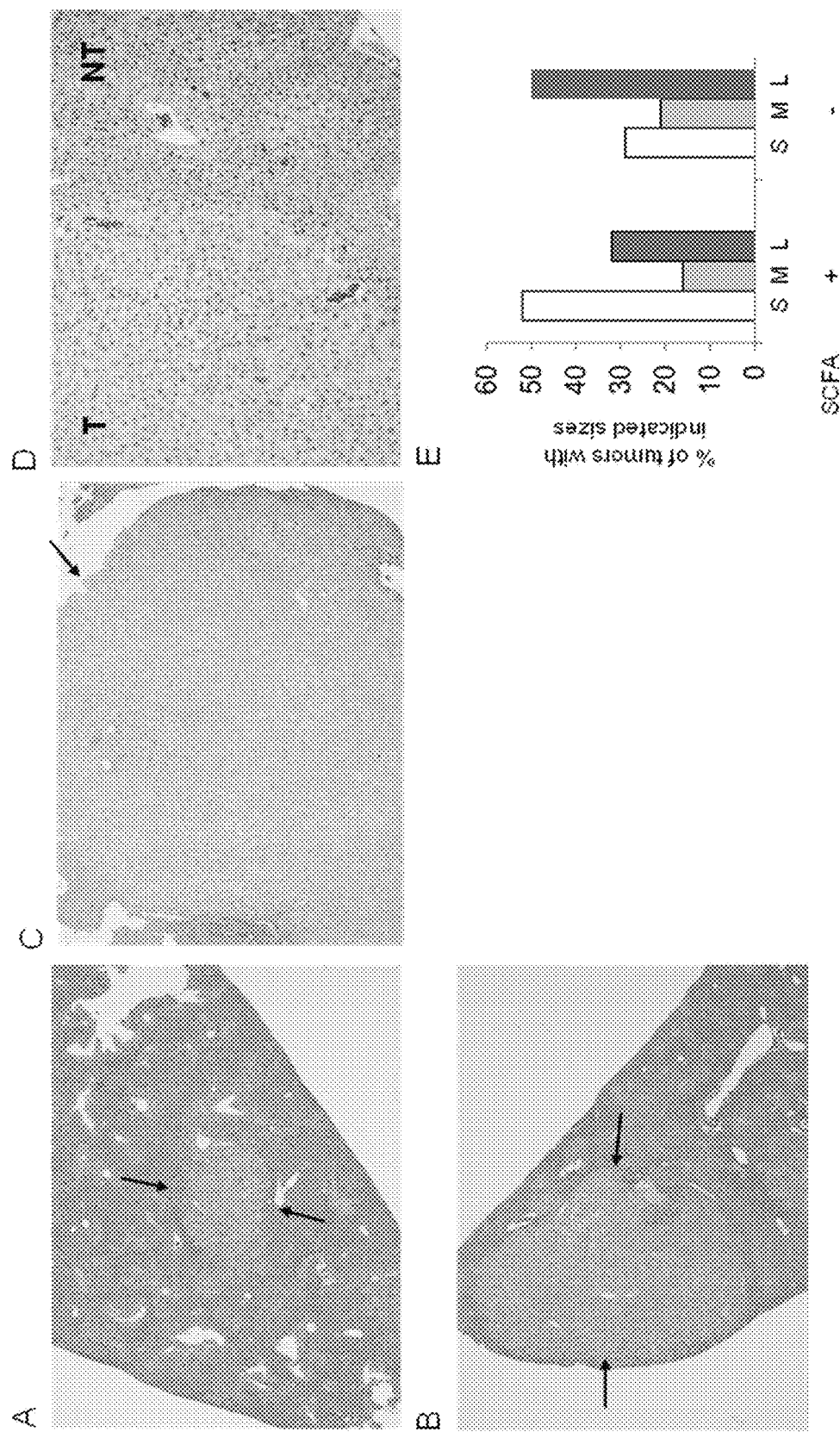
FIG. 6A-6E depicts H&E stained liver sections and a bar graph showing the characteristics of tumors in SCFA fed mice. HBx mice were treated with SCFAs or PBS for three months starting at nine months of age.

The lactic acid producing bacteria in Synbiotic 2000™ are supplied with a rich source of prebiotic nutrients that are metabolized to SCFAs. SCFAs are known to be anti-inflammatory, and since HCC arises on a background of chronic liver disease that has an inflammatory component, experiments were designed to determine whether SCFAs would have the same impact upon the pathogenesis of HCC as did Synbiotic 2000™. Since the greatest impact of Synbiotic 2000™ was observed among 9-12 month old mice that were developing HCC, 9 month old mice were fed SFCAs by gavage for 3 months and then their livers examined for the presence, frequency and distribution of lesions. When the livers were removed from SCFA treated mice at 12 months of age, tumors on the surface of the liver were more numerous and larger among PBS treated compared to SCFA treated mice (FIG. 5). When microscopic sections were prepared from each lobe and tumor sizes evaluated again, 52% of the tumors present were small (<0.5 cm in diameter) while 32% were large (>1 cm in diameter). In contrast, among placebo treated mice, only 29% were small, but 50% were considered large (FIG. 6; X2=4.59, P<0.05). This is also reflected in the ratio of large:small tumors in the two groups of mice. Among placebo treated mice, the ratio was 1.75, but among SCFA treated mice, the ratio shifted to 0.62, suggesting that SCFA partially blocked the development of large tumors. In all mice, the tumor morphology was characteristic of undifferentiated HCC, independent of tumor size (FIG. 6D).

HCC is a major public health problem, especially in developing countries where HBV is endemic. It is diagnosed late in most cases which makes this tumor type difficult to treat. This provides strong rationale for the development and application of intervention strategies that could be used to treat patients with early stage cancer or precancerous lesions. The results herein demonstrate that even 3 months of treatment with selected lactic acid bacteria, or a mixture of their SCFA metabolites, there is a significant reduction in the number and size of HCC nodules that appear in HBx transgenic mice.

HBx transgenic mice undergo progressive development of liver lesions with age, culminating in the appearance of HCC by 10 months (Yu D Y et al., J Hepatol, 1999; 31:123-132). Treatment of mice with Synbiotic 2000™ from 6-9 months of age strongly reduced the incidence of dysplasia (FIG. 2B), while mice treated from 9-12 months of age had a significantly reduced incidence of HCC (FIG. 2C). Given that dysplasia develops during the period from 6-9 months of age, and HCC develops from 9-12 months, these findings suggest that Synbiotic 2000™ prevents the progression of chronic liver disease to preneoplastic and tumor nodules. This interpretation is also consistent with the observation that steatosis and dysplasia, which are well established by 9 months of age, are not affected by Synbiotic 2000™ treatment started at that age (FIG. 2C).

Figures 3A, 3B, 3C, 3D:
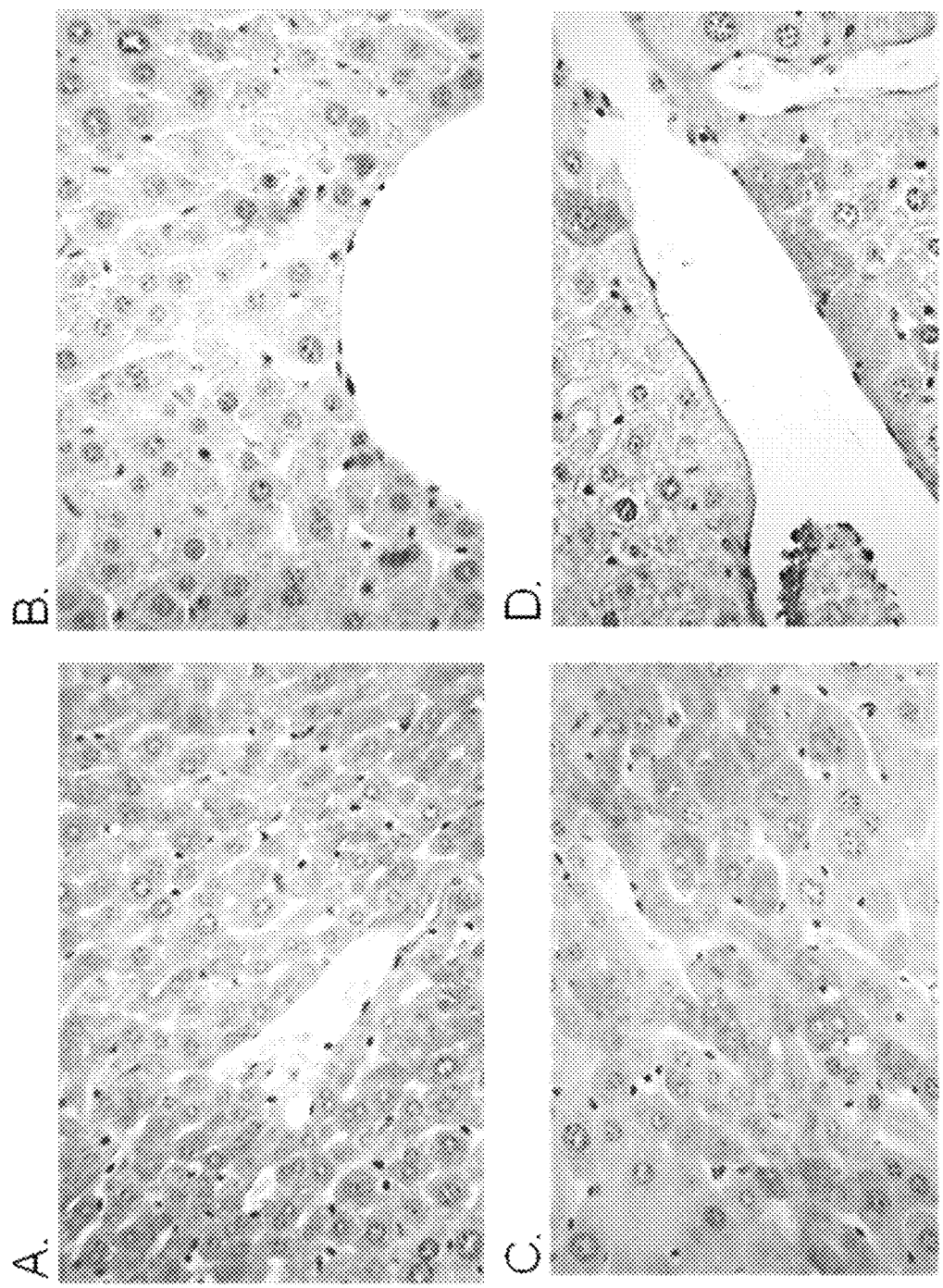
FIG. 3A-3D depicts HBx staining in the liver of a 6 month old (FIG. 3A) and 9 month old (FIG. 3C) mouse liver following treatment with PBS (FIG. 3A and FIG. 3C) or Synbiotic 2000™ (FIGS. 3B and 3D). Note that in both cases, lobular distribution of HBx gives rise to a more scattered distribution following treatment with Synbiotic 2000™, suggesting that HBx levels may be decreased with treatment.
Figure 4:
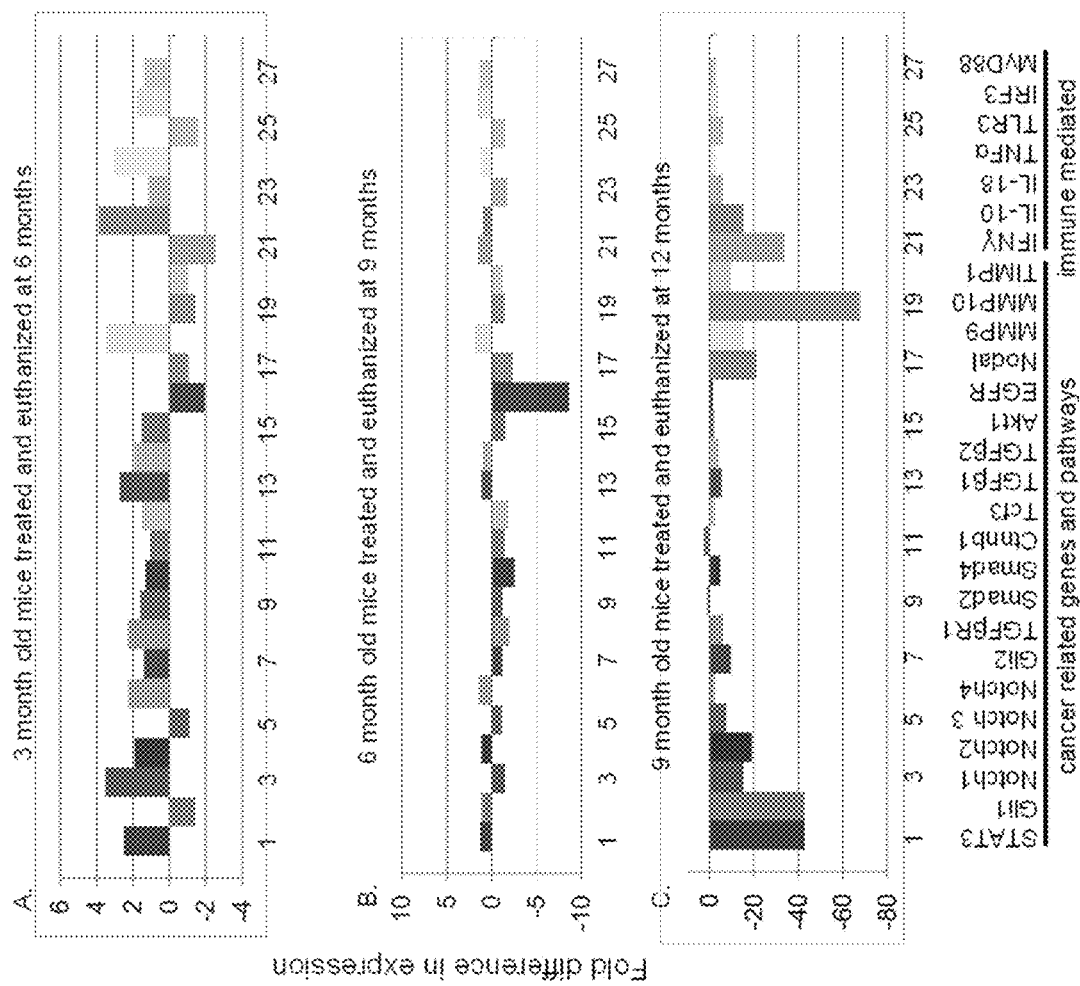
FIG. 4 depicts graphs of limited microarray analysis showing expression of selected markers of carcinogenesis (columns 1-20) and immune mediators (columns 21-27) in HBx transgenic mice given Synbiotic 2000™ at the indicated ages compared to HBx transgenic mice give placebo in parallel. Values for differential expression were normalized with GAPDH. Other controls included one for genomic DNA contamination (MGDC), another for RNA quality (RTC), and another for general PCR performance (PPC).

In the HBx transgenic mice, the intrahepatic levels of HBx increase with age and the severity of the underlying liver pathology (FIGS. 3A and 3C). This is consistent with the strong association between the expression of X protein and progressive chronic liver disease in both human and woodchuck carriers with chronic liver disease (Jin Y M et al., J Viral Hepat, 2001; 8(5):322-30; Feitelson M A et al., J Hepatol, 1993; 17 (Suppl. 3):S24-S34). HBx activity is potentiated in the presence of reactive oxygen species (ROS) (Wang J H et al., Biochem Biophys Res Commun, 2003; 310(1):32-9; Lim W et al., Mol Med (Berl), 2010; 88(4): 359-69) provided by cellular immune responses within the inflammatory infiltrates of the liver. Under these circumstances, HBx trans-activates its own enhancer/promoter (which is also part of the transgene in these HBx transgenic mice), resulting in increased levels of HBx expression. A small amount of HBx is also known to be associated with mitochondria, where it compromises the electron transport chain, resulting in the further accumulation of ROS (Fatima G et al., J Gen Virol, 2012; 93(Pt 4):706-15). In this context, it is known that lactic acid producing bacteria and their SCFA metabolic products stimulate T regulatory cells in the gut and beyond (Smith P M et al., Science, 2013; 341(6145): 569-73), which could limit inflammatory responses and ROS production, thereby decreasing the activity and intrahepatic levels of HBx (FIG. 3). This is also consistent with the results of limited microarray analysis where a number of immune based markers were down-regulated in mice treated with Synbiotic 2000™ (FIG. 4). Previous work has shown that intrahepatic ROS increased in HBV carriers and in HBx transgenic mice with progressive chronic liver disease (Ha HL, et al., World J Gastroentero, 2010; 16(39):4932-7). When a sampling of immune markers was evaluated in progressively older mice, treatment with Synbiotic 2000™ had the largest effect (i.e., down-regulation of these immune markers) among the oldest mice with the highest levels of intrahepatic ROS (FIG. 4). Since the levels and activity of HBx are, in part, ROS dependent, and HBx drives tumor development in these animals, this may explain the correlation between decreased HBx expression (FIG. 3, FIG. 10) and the decreased incidence of dysplasia and HCC in mice treated with Synbiotic 2000™ (FIGS. 8 and 9, FIG. 2).

HBx activates the expression of genes in multiple pathways that contribute importantly to hepatocarcinogenesis. Their suppression among 9 month old mice treated with Synbiotic 2000™ supports the hypothesis that this intervention partially blocks the ability of HBx to promote tumor development (FIG. 4). For example, HBx mediated activation of hedgehog signaling via up-regulation of Gli 1 and 2 (Arzumanyan A et al., Cancer Res, 2012; 72(22):5912-5920), are strongly down-regulated by Synbiotic 2000™ by more than 40-fold and 7-fold, respectively (FIG. 4C). Treatment of HBx transgenic mice with the canonical hedgehog inhibitor, GDC-0449, also decreased the number and size of tumors that appeared in HBx transgenic mice (Arzumanyan A et al., Cancer Res, 2012; 72(22):5912-5920), underscoring the importance of hedgehog signaling to HCC. Notch signaling, which is also up-regulated by HBx (Wang F et al., Cancer Lett, 2010; 298(1):64-73), was also depressed an average of more than 10-fold after Synbiotic 2000™ treatment (FIG. 4C). Since Notch contributes to cell fate during embryogenesis, its reactivation in carcinogenesis may also mediate steps that convert normal to tumor cells. A parallel argument could be made for Nodal, which is down-regulated more than 20-fold in 9 month old mice treated with Synbiotic 2000™. HBx activation of β-catenin, which is important to hepatocarcinogenesis, is not activated in Synbiotic 2000™ treated mice developing HCC (FIG. 4C). Given that β-catenin is a "stemness" associated protein, and that HBx promotes HCC, at least in part, through up-regulated expression of "stemness" markers, inhibition of b-catenin activation by Synbiotic 2000™ may block the expansion of hepatic and/or cancer stem cells in the liver. TGFβ signaling, also up-regulated by HBx, is essentially extinguished by Synbiotic 2000™ treatment initiated in 9 month old mice (FIG. 4C). Given that HBx shifts TGFβ signaling from a negative to a positive regulator of hepatocellular growth, inhibition of this pathway would partially prevent HBx from promoting tumor development. In addition, the fact that Synbiotic 2000™ treatment strongly inhibited MMP-9 (by 15-fold) and MMP-10 (by more than 65-fold) (FIG. 4C), which are otherwise up-regulated by HBx (Liu L P et al., Cancer Invest, 2010; 28(5):443-51; Sze K M et al., Hepatology, 2013; 57(1):131-9) and promote cancer spread by metastasis, suggests additional pathways whereby this treatment approach may block the progression of lesions in the liver to dysplasia and HCC.

The role of NF-κB, which is activated by HBx in the presence of ROS, seems to provide a common denominator for many of the observed effects of Synbiotic 2000™ upon liver pathology and the associated molecular changes. For example, down-regulation of Notch signaling is accompanied by the down-regulation of NF-κB activity in hepatocarcinogenesis (Luo J et al, Int J Oncol, 2013; 42(5):1636-43). Notch inhibition also results in the inhibition of β-catenin activity (Sun Q et al., Int J Oncol. 2014), suggesting cross-talk among these pathways in the development of HCC. HBx activation of NF-κB also up-regulates the expression and activity of MMP-9 which promotes tumor metastasis (Liu L P et al., Cancer Invest, 2010; 28(5):443-51). Interestingly, HBx up-regulation of IL-6 in a MyD88 (and NF-κB) dependent manner (Xiang W Q et al., J Hepatol, 2011; 54(1):26-33). Upon binding to its receptor, IL-6 results in activation (phosphorylation) of STAT3, which in turn activates a variety of genes including STAT3 itself Unphosphorylated STAT3 then binds to NF-κB, resulting in altered expression of additional selected cellular genes that contribute to HCC (Yang J et al., Genes Dev, 2007; 21(11):1396-408). Further, mediators of inflammation, such as TLR3, IL-18, TNFα, TGFβ, MyD88, and IRF3 also signal downstream through NF-κB, suggesting that an anti-inflammatory environment set up by Synbiotic 2000™ treatment would be expected to decrease expression and/or signaling through these molecules, and this is what appears to be happening in these mice (FIG. 4C). TLR3 and IL-18 levels are decreased by 6-fold, TNFα and MyD88 by 3-fold, TGFβ by more than 5-fold, and IRF3 by almost 4-fold. These findings suggest that the reduction in ROS, and subsequent inactivation of NF-κB, may be an important strategy in cancer chemoprevention.

SCFAs are major metabolic products of lactic acid producing bacteria that promote T-cell differentiation into both effector and regulatory T cells to promote either immunity or immune tolerance (Park J et al., Mucosal Immunol, 2014). In this study, it appears that tolerance is favored. SCFA treatment recapitulated the results of Synbiotic 2000™ treatment in the prevention of HCC (FIGS. 5 and 6) Administration of butyrate helped to resolve chemically induced colitis (Smith P M et al., Science, 2013; 341(6145):569-73; Celasco G et al., Biomed Rep, 2014; 2(4):559-563) and partially blocked DEN induced HCC (Kuroiwa-Trzmielina J et al., Int J Cancer, 2009; 124(11):2520-7; de Conti A et al., J Nutr Biochem, 2012; 23(8):860-6), while proprionate has been shown to reduce the growth of an established tumor (Bindels L B et al., Br J Cancer, 2012; 107(41337-44) in mouse models. Thus, SCFAs may be of value in blocking tumor development and progression. The anti-inflammatory properties of the SCFAs may reflect their function by binding to G-protein coupled receptors (GPCRs) and as HDACi (Tan J et al., Adv Immunol, 2014; 121:91-119). Given that HBx activation of hedgehog and Win signaling occur though GPCR related pathways (where Smoothened and Frizzled are GCPRs) (Dorsam R T et al., Trends Pharmacol Sci, 2013; 34(4):226-32), it is possible that the alteration of GPCR signaling by SCFAs could alter or partially block the signaling activated by HBx, as it does for other cancers. In addition, the finding that HBx activates HDAC expression (Tian Y et al., Mol Cell Biol, 2013; 33(15):2810-6), and that SCFAs act as HDACi, suggests that key pathways that contribute to carcinogenesis could be blocked by SCFAs. Finally, it is important to consider that the impact of Synbiotic 2000™ and SCFA treatment may go far beyond the mechanisms outlined above, since the decrease in HBx expression with treatment (FIG. 3) may also suppress the ability of HBx to mediate other epigenetic changes in gene expression, such as DNA and protein methylation, protein phosphorylation, ubiquitination, sumoylation, as well as other post-translational modifications that contribute to carcinogenesis (Mann D A, Hepatology, 2014).

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for decreasing liver inflammation in a subject in need thereof, the method comprising administering to the subject a therapeutically effective amount of a composition comprising at least one short chain fatty acid or a pharmaceutically acceptable salt thereof; wherein the composition is administered orally as an oral dosage form.

2. The method of claim 1, wherein the short chain fatty acid is selected from the group consisting of: formic acid, acetic acid, propionic acid, isobutvric acid, butyric acid, isovaleric acid, valeric acid, isocaproic acid, caproic acid, lactic acid, succinic acid, and pyruvic acid.

3. The method of claim 1, wherein said composition further comprises a pharmaceutically acceptable excipient.

4. The method of claim 1, wherein said composition is administered in combination with another therapeutic agent.

5. The method of claim 1, wherein the composition is administered with food or drink.

6. The method of claim 1, wherein decreasing liver inflammation treats liver disease in the subject.

7. The method of claim 1, wherein decreasing liver inflammation delays onset of hepatocellular cancer in the subject.

8. The method of claim 1, wherein decreasing liver inflammation is by modulating expression of a mediator of inflammation.

9. The method of claim 8, wherein the mediator of inflammation is TNF-α.

10. The method of claim 9, wherein the administering decreases expression of TNF-α.

11. The method of claim 8, wherein the mediator of inflammation is TLR3.

12. The method of claim 8, wherein the mediator of inflammation is IL-18.

13. The method of claim 8, wherein the mediator of inflammation is MyD88.

14. The method of claim 8, wherein the mediator of inflammation is TGFβ.

15. The method of claim 8, wherein the mediator of inflammation is IRF3.

16. The method of claim 1, wherein the short chain fatty acid is butyric acid or a pharmaceutically acceptable salt thereof.

17. The method of claim 16, wherein the composition further comprises propionic acid or a pharmaceutically acceptable salt thereof.

* * * * *